(12) United States Patent
Campbell et al.

(10) Patent No.: US 8,374,553 B1
(45) Date of Patent: Feb. 12, 2013

(54) METHOD AND SYSTEM FOR IMPROVING A COMMUNICATION RANGE AND RELIABILITY OF A SOIL SENSOR ANTENNA

(75) Inventors: Jeffrey Campbell, Boise, ID (US); Kathy Sohrabi, San Diego, CA (US); Clayton R. Karmel, San Diego, CA (US)

(73) Assignee: Green Badge, LLC, King Of Prussia, PA (US)

( * ) Notice: Subject to any disclaimer, the term of this patent is extended or adjusted under 35 U.S.C. 154(b) by 529 days.

(21) Appl. No.: 12/697,258

(22) Filed: Jan. 31, 2010

Related U.S. Application Data

(60) Provisional application No. 61/149,692, filed on Feb. 3, 2009.

(51) Int. Cl.
*H04B 7/00* (2006.01)

(52) U.S. Cl. ............ 455/66.1; 702/22; 702/2; 250/255; 356/366; 356/337; 356/303; 356/326; 700/284; 137/78.3

(58) Field of Classification Search ............... 455/66.1; 702/22, 2; 250/255; 356/366, 337, 303, 356/326; 700/284; 137/78.3
See application file for complete search history.

(56) References Cited

U.S. PATENT DOCUMENTS

| | | | |
|---|---|---|---|
| 4,256,133 A | 3/1981 | Coward et al. | |
| 4,396,149 A | 8/1983 | Hirsch | |
| 4,684,920 A | 8/1987 | Reiter | |
| 4,785,843 A | 11/1988 | Nicholson | |
| 5,839,660 A | 11/1998 | Morgenstern et al. | |
| 6,937,939 B1 * | 8/2005 | Shibusawa et al. | 702/22 |
| 6,947,810 B2 | 9/2005 | Skinner | |
| 6,963,205 B2 | 11/2005 | Lundstrom et al. | |
| 7,063,270 B2 | 6/2006 | Bowers et al. | |
| 7,184,892 B1 | 2/2007 | Dyer et al. | |
| 7,203,576 B1 * | 4/2007 | Wilson et al. | 700/284 |
| 7,264,177 B2 | 9/2007 | Buck et al. | |
| 7,318,010 B2 | 1/2008 | Anderson | |
| 7,413,380 B2 | 8/2008 | Corwon et al. | |
| 8,245,720 B2 * | 8/2012 | Grill et al. | 137/78.3 |
| 2007/0237583 A1 | 10/2007 | Corwon et al. | |
| 2009/0099701 A1 | 4/2009 | Li et al. | |
| 2009/0276102 A1 | 11/2009 | Smith et al. | |
| 2010/0194411 A1 | 8/2010 | Caron | |

* cited by examiner

*Primary Examiner* — April G Gonzales
(74) *Attorney, Agent, or Firm* — Clause Eight IPS; Michael Catania

(57) ABSTRACT

A wireless sub-surface soil sensor having a switchable configuration antenna that can be optimized for various soils is disclosed herein. The wireless sub-surface sensor also measures the moisture and salinity of a material. The wireless sub-surface sensor preferably includes a cover for protecting circuitry of the sensor. The wireless soil sensor is designed to be buried underground and to transmit to above ground receivers, which provide feedback for configuring the switchable antenna.

10 Claims, 25 Drawing Sheets

METHOD AND SYSTEM FOR IMPROVING A COMMUNICATION RANGE AND RELIABILITY OF A SOIL SENSOR ANTENNA

CROSS REFERENCE TO RELATED APPLICATION

The present application claims priority to U.S. Provisional Patent Application No. 61/149,692, filed on Feb. 2, 2009, which is hereby incorporated by reference in its entirety.

STATEMENT REGARDING FEDERALLY SPONSORED RESEARCH OR DEVELOPMENT

Not Applicable

BACKGROUND OF THE INVENTION

1. Field of the Invention

The present invention is related to a method and system for improving a communication range and reliability of a wireless sub-surface sensor antenna.

2. Description of the Related Art

The prior art discusses other irrigation systems and methods.

Closing an underground to above ground RF communication link is a challenging task. The challenge is typically due to difficult propagation conditions perpetrated by high water content as well as high conductivity in the soil.

The moisture and conductivity vary over time depending on environmental stimulus. High water content increases the rate of absorption of RF energy. Salinity and moisture both change the die-electric constant of the soil, effectively detuning the antenna element as water content changes over time.

In instances, it is possible to adaptively modify the antenna tuning elements, to attempt to tune the antenna to the current state of the soil.

However, in some instances it may not be possible to overcome the adverse effects of moisture in the ground by direct tuning of the RF and antenna components on board the underground wireless sensor. In other instances, certain wireless sensing devices may not be able to adapt their tuning in close to real time to match the soil conditions.

The Present Invention seeks to resolve the problems of the prior art.

BRIEF SUMMARY OF THE INVENTION

The present invention provides a solution to the problems of the prior art. The inventors of the present invention noticed the dielectric of soil, and how it changes with moisture and salinity, which led them to believe that a radiofrequency ("RF") antenna of a wireless sub-surface soil sensor may be able to be tuned based on moisture and salinity measurements. The inventors measured soil moisture and salinity using novel sensors which also provided the electrical properties of the soil in which the wireless sub-surface soil sensor was placed. These electrical properties affect the efficient transmission and range of an antenna. The inventors realized that an antenna could be configured to optimize transmission efficiency and boost range. Components added to the antenna circuitry controlled by the processor allow for the antenna to be tuned based on the electrical properties of the soil.

RF impedances (complex resistances) are often characterized on a two dimensional SMITH® Chart. A discussion of SMITH® Charts is set forth in *Designing Impedance Matching Networks With the HP 8751A*, Hewlett-Packard Company, 1990, which is hereby incorporated by reference in its entirety. Another discussion of SMITH® Charts is set forth in Stephen D Stearns, *Mysteries of the Smith Chart*, Pacificon 2001, 2001, which is hereby incorporated by reference in its entirety. The inventors noticed that if the antenna is tuned in a specific and novel manner, its impedance is shifted in an arc around the ideal match (about 50 ohms) as moisture levels in the soil changed. By characterizing the arc by a radius and angle, the inventors were able to tune the radius to remain nearly constant. Only the phase angle of the impedance changed. The inventors designed the physical antenna structure, board structure, housing (air space) and tuning elements to maintain a constant impedance magnitude. This became an automatic, adaptive RF tuning which improved antenna performance across a range of soil moisture levels.

One aspect of the present invention is a wireless soil sensor. The wireless soil sensor is preferably capable of measuring soil moisture, soil salinity and soil temperature, while buried beneath the surface and also capable of wirelessly transmitting the measurements to a receiver above the surface for eventual transmission to an engine for calculations and other outputs.

The wireless soil sensor preferably has a tine sleeve for placement over a portion of the sensor. The sleeve is removed when the sensor is ready to be buried beneath the surface of the soil.

The sensor preferably links to a controller, is preferably associated with a watering zone which is to be controlled by a controller. At least a portion of the sensor is preferably waterproof. The tine sleeve preferably has a small patch of exposed PCB conductor which is connected to another, which allows the sensor to assume it is in a hibernation state (for power savings, suppressed communications and suppressed emissions). Essentially, while the sensor has the tine sleeve attached, it is in an inactive state.

The tine sleeve further protects the sensitive components of the sensor during shipment.

Removal of the tine sleeve is an intuitive indication that the sensor is to be associated and buried. The sensor assumes a period of active communication so that a controller/interrupter can learn of its presence and prompt assignment to a watering zone or zones.

After a set period of time, the sensor preferably assumes a normal sensing and broadcast mode. The tine sleeve further acts a physical receipt, allowing for marking with the date, position of installation and corresponding watering zones. The tine sleeve further provides the function of enabling safe transportation of the end-of-life or return for repair of the sensor to a factory or alternative site.

The wireless sensor preferably infers moisture and salinity levels by measuring the dielectric constant of the surrounding soil. A radio antenna used to relay these measurements to a central controller is affected (de-tuned) by surrounding changes in the dielectric constant. The present invention can adaptively tune the antenna impedance match via RF switches and passive components based on moisture and salinity readings. This increases the communication range and reduces power consumption.

A user interface for an irrigation interrupter preferably has a default display of 128 by 64 pixel. In a limited space, the display communicates a tremendous amount of information in an extremely intuitive way. Six columns for watering zones are used in the display. Each zone shows a moisture assessment of Ok, Wet, Dry, or Cold. Next to this is a visual indication of the moisture level in the zone, as reported by one or more sensors, adapted to a soil/plant type. A bar showing moisture level preferably has two marks indicating a lower level where no watering would be interrupted, an upper level indicating that all watering would be interrupted, and in the zone in between, a sensor for how much of the normal watering period will be allowed before a mid-flow cutoff attenuates watering. A bold OFF and ON indication blinks between the view and the underlying moisture status normally shown. The blinking behavior is set to occur when a zone input is active, and indicates the action being taken by the interrupter. Above the moisture indications is a row showing the control status of each zone-whether it is controlled by one or more sensors, or has been placed in manual ON or manual OFF. The user interface allows for determination of a manual mode with only a casual view of the user interface. The top line shows the system status (Auto, Bypass, Master, Slave) and the recent average of water saving, calculated by the percentage of time normally watering has been attenuated. Master and Slave are used to enable "chaining" of multiple interrupters together to control additional zones, preferably six at a time. At the bottom of the display, icons show whether one or more than one sensor is assigned per zone. A solid square is a sensor with no performance issues. A hollow square indicates low battery. A triangle indicates RF reception issues. A hollow triangle represents RF reception and battery issues.

In such conditions, where information about soil moisture and salinity conditions at the time of attempted transmission is available to the wireless sensor, for example when there are on board moisture and conductivity sensor present, the wireless transmitter will perform a simple computation to determine whether its transmission will be successful given the network activity history and the soil moisture and conductivity levels. The wireless sensor will track the moisture and conductivity levels, and based on those levels will adjust its transmission attempts. The impact of this decision making is that it will predict when the transmission will fail, and thus refrain from transmitting. This adaptive adjustment of the transmission schedule will help conservation battery life for battery operated sensor nodes. This adaptive schedule will be effective for one way as well as two way communication links. However its impact will be most evident for two-way over the air protocols.

It is an object of the present invention to provide a proprietary wireless root zone intelligence system that measures real time soil moisture, temperature and salinity. It is an object of the present invention to provide an advanced wireless sensor and analytical, intuitive, fully interactive software. It is an object of the present invention to optimize turf health and playability, improve product quality, optimize resource utilization.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL
VIEWS OF THE DRAWINGS

FIGS. 14-1 is a graph of soil temperature for a number of days to demonstrate that without an understanding of the overall conditions the temperature data is a minimal value.

FIGS. 14-2 is a graph of soil moisture for a number of days to demonstrate that without an understanding of the overall conditions the temperature data is a minimal value.

FIGS. 14-3 is a graph of soil salinity for a number of days to demonstrate that without an understanding of the overall conditions the temperature data is a minimal value.

FIGS. 14A-1 is a graph of soil temperature for a number of days to demonstrate the benefit of knowing the overall conditions and defining a zone for optimum performance.

FIGS. 14A-2 is a graph of soil moisture for a number of days to demonstrate the benefit of knowing the overall conditions and defining a zone for optimum performance.

FIGS. 14C-1 is a graph of soil salinity for a number of days to demonstrate good quality irrigation.

FIGS. 14C-2 is a graph of soil salinity for a number of days to demonstrate poor quality irrigation.

DETAILED DESCRIPTION OF THE INVENTION

The present invention is preferably used with a system and method such as disclosed in Glancy, et al., U.S. Patent Publication Number 2006/0178847 for an Apparatus And Method For Wireless Real Time Measurement And Control Of Soil And Turf Conditions, which is hereby incorporated by reference in its entirety.

The present invention may be used with a system, sensor and method such as disclosed in Campbell, U.S. Pat. No. 7,482,820 for a Sensor For Measuring Moisture And Salinity, which is hereby incorporated by reference in its entirety. The present invention may use a chemical sensor probe such as disclose in U.S. Pat. No. 4,059,499 which is hereby incorporated by reference in its entirety. The present invention may use a chemical sensor probe such as disclose in U.S. Pat. No. 5,033,397 which is hereby incorporated by reference in its entirety. Systems and methods for optimizing irrigation are disclosed in Magro et al., U.S. patent application Ser. No. 12/697,226, filed on Jan. 30, 2010, for a Method And System For Monitoring Soil And Water Resources, which is hereby incorporated by reference in its entirety. Systems, methods, sensors, controllers and interrupters for optimizing irrigation are disclosed in Campbell et al., U.S. patent application Ser. No. 12/697,254, filed on Jan. 31, 2010, for a Method And System For Soil And Water Resources, which is hereby incorporated by reference in its entirety.

A wireless sub-surface sensor 21 is shown in FIGS. 1-8. The wireless sub-surface sensor is placed in the soil below the surface to monitor various parameters of the soil such as electrical properties. Other parameters include moisture, salinity and temperature.

Figure 1:
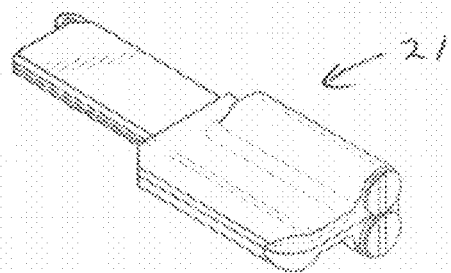
FIG. 1 is a top perspective view of a wireless soil sensor of the present invention with a sleeve attached over a portion of the wireless soil sensor.
Figure 2:
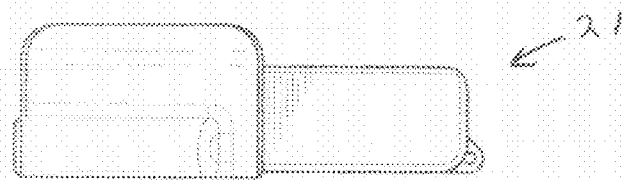
FIG. 2 is a first side view of the wireless soil sensor of FIG. 1.
Figure 3:
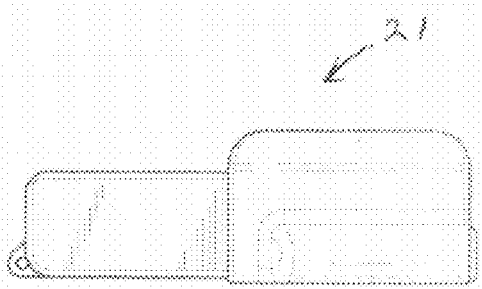
FIG. 3 is an opposing side view of the wireless soil sensor of FIG. 1.
Figure 4:
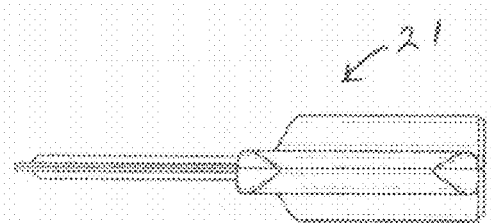
FIG. 4 is top plan view of the wireless soil sensor of FIG. 1.
Figure 5:
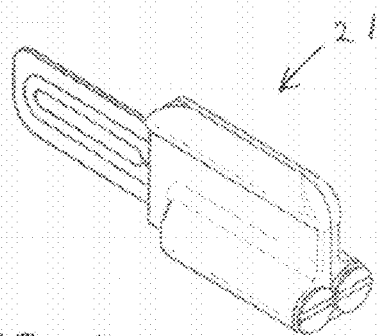
FIG. 5 is a top perspective view of a wireless soil sensor of the present invention without a sleeve attached over a portion of the wireless soil sensor.
Figure 6:
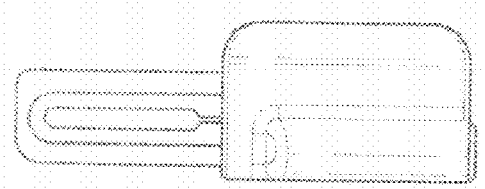
FIG. 6 is a first side view of the wireless soil sensor of FIG. 5.
Figure 7:
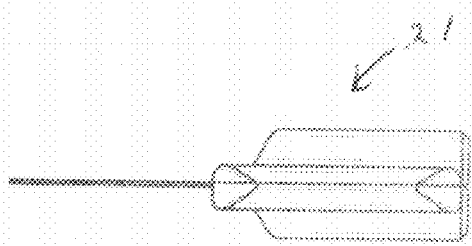
FIG. 7 is top plan view of the wireless soil sensor of FIG. 5.
Figure 8:
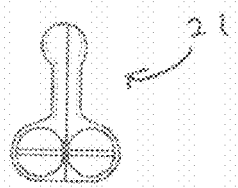
FIG. 8 is a rear plan view of the wireless soil sensor of FIG. 5.
Figure 9:
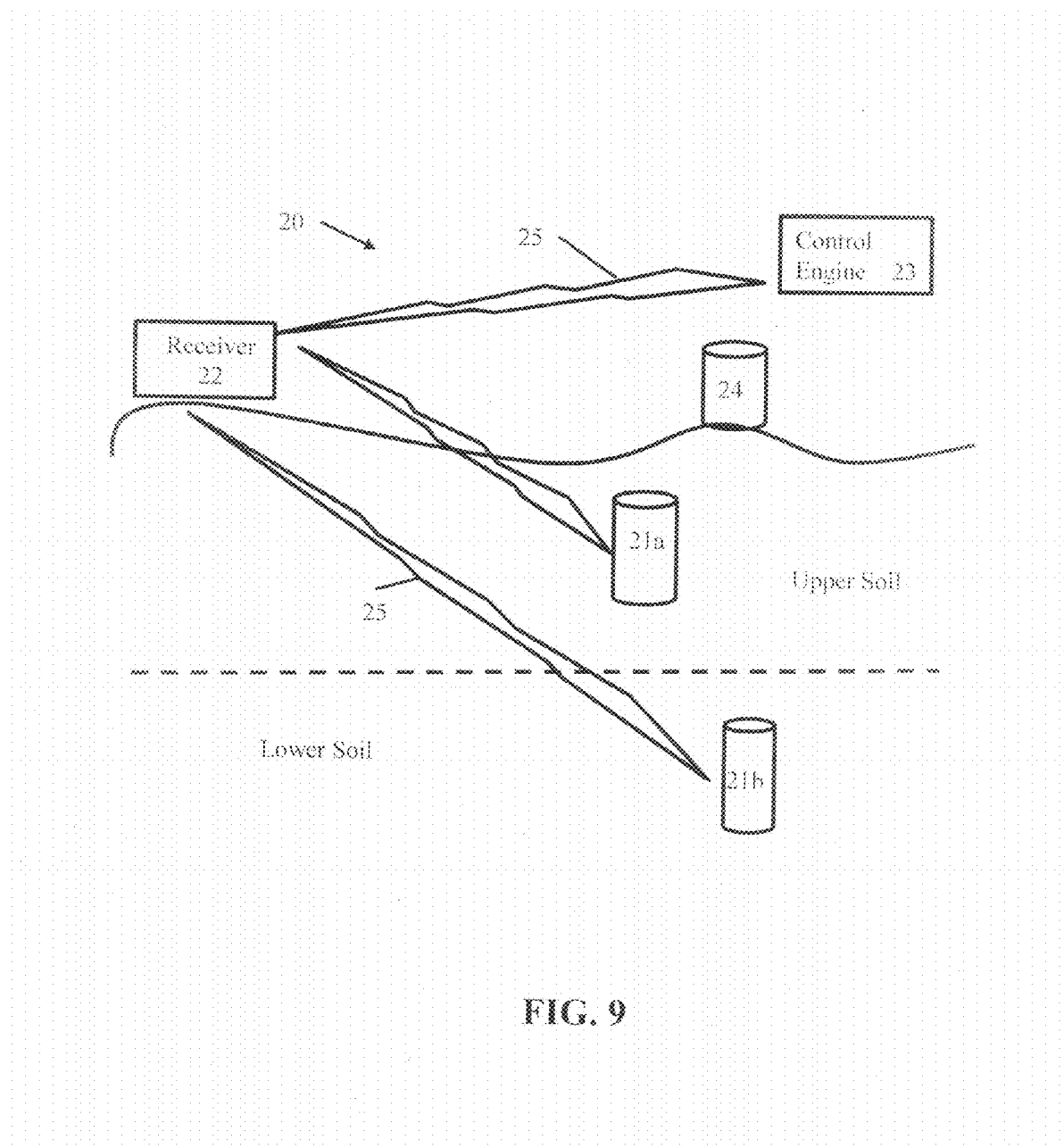
FIG. 9 is a schematic diagram of a preferred embodiment of a system of the present invention.
Figure 9A:
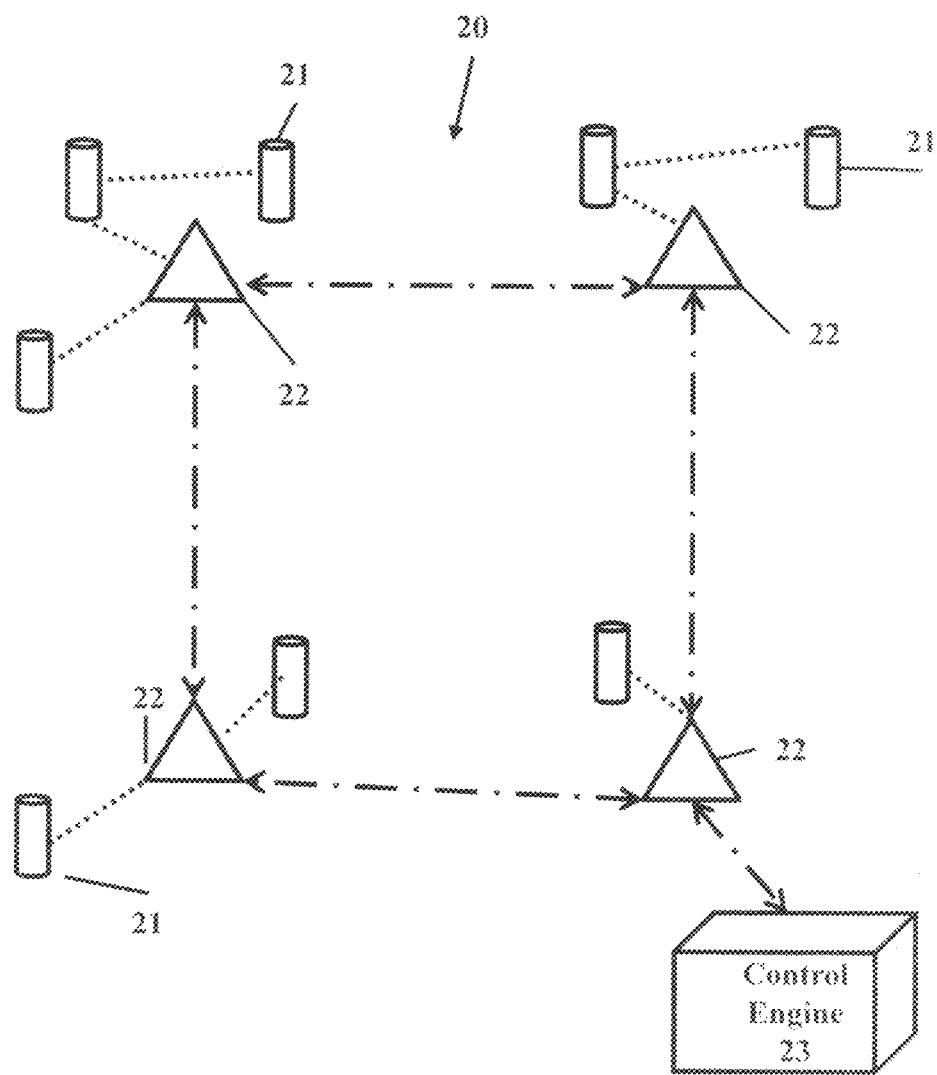
FIG. 9A is a schematic diagram of a preferred embodiment of a system of the present invention illustrating a mesh network established by the transmitters of the system.
Figure 9B:
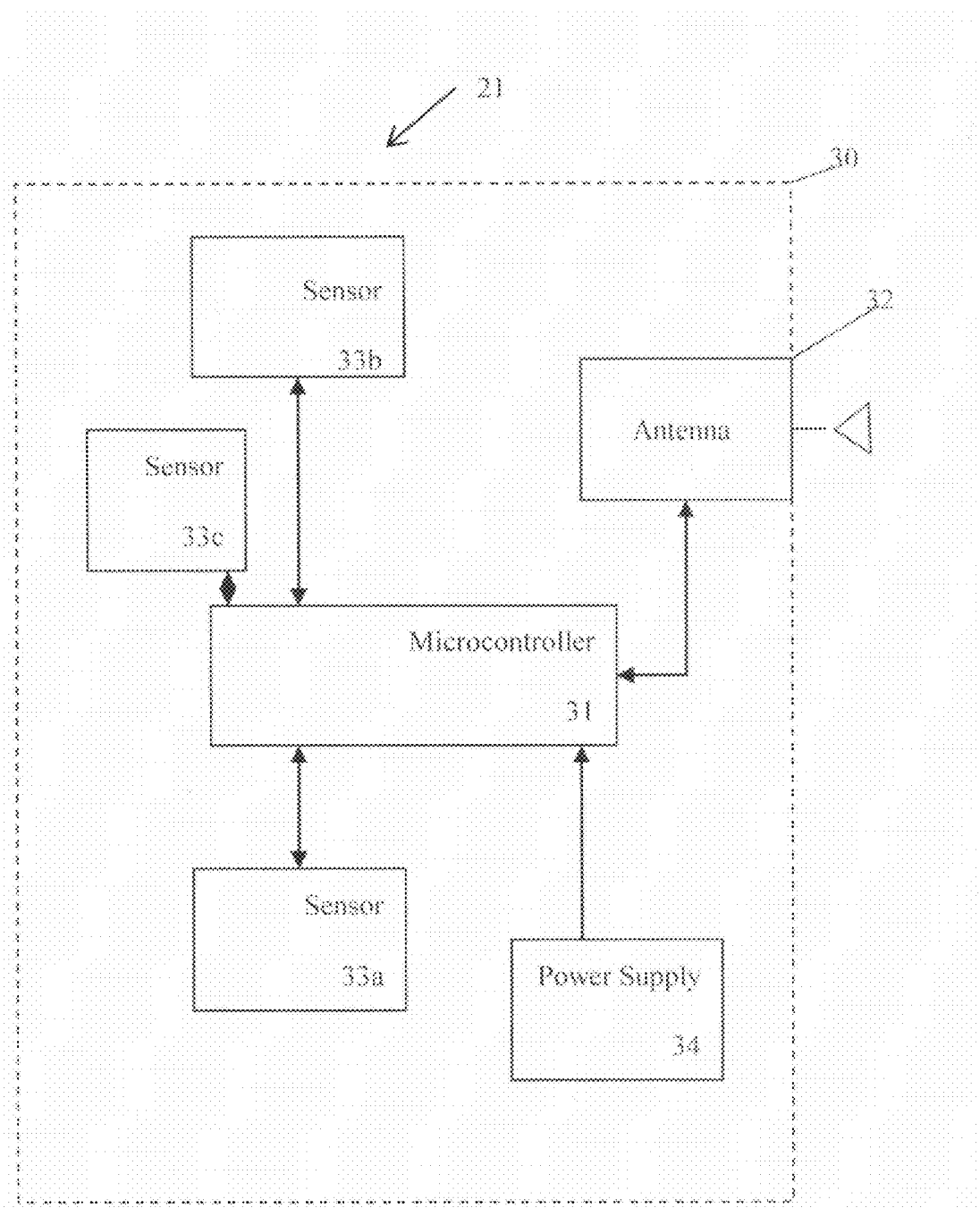
FIG. 9B is a schematic diagram of a preferred embodiment of a sensor node of the system.

As shown in FIGS. 9, 9A and 9B, a preferred embodiment of a system of the present invention is generally designated 20. The system preferably includes a plurality of wireless sub-surface sensors 21 (upper soil 21a and lower soil 21b), a plurality of above-ground receivers 22, a control engine located at an operations center, and a plurality of above-ground sensors 24. The above ground sensors 24 preferably measures air temperature, wind speed, and relative humidity.

FIG. 9B illustrates a wireless sub-surface sensor 21 preferably utilized in the system 20. The wireless sub-surface sensor 21 preferably has a housing 30, a processor 31, a configuration switchable antenna 32, sensors 33a, 33b and 33c, and a power supply 34. The sensors 33 are preferably measure the electrical properties of the soil.

Figure 9C:
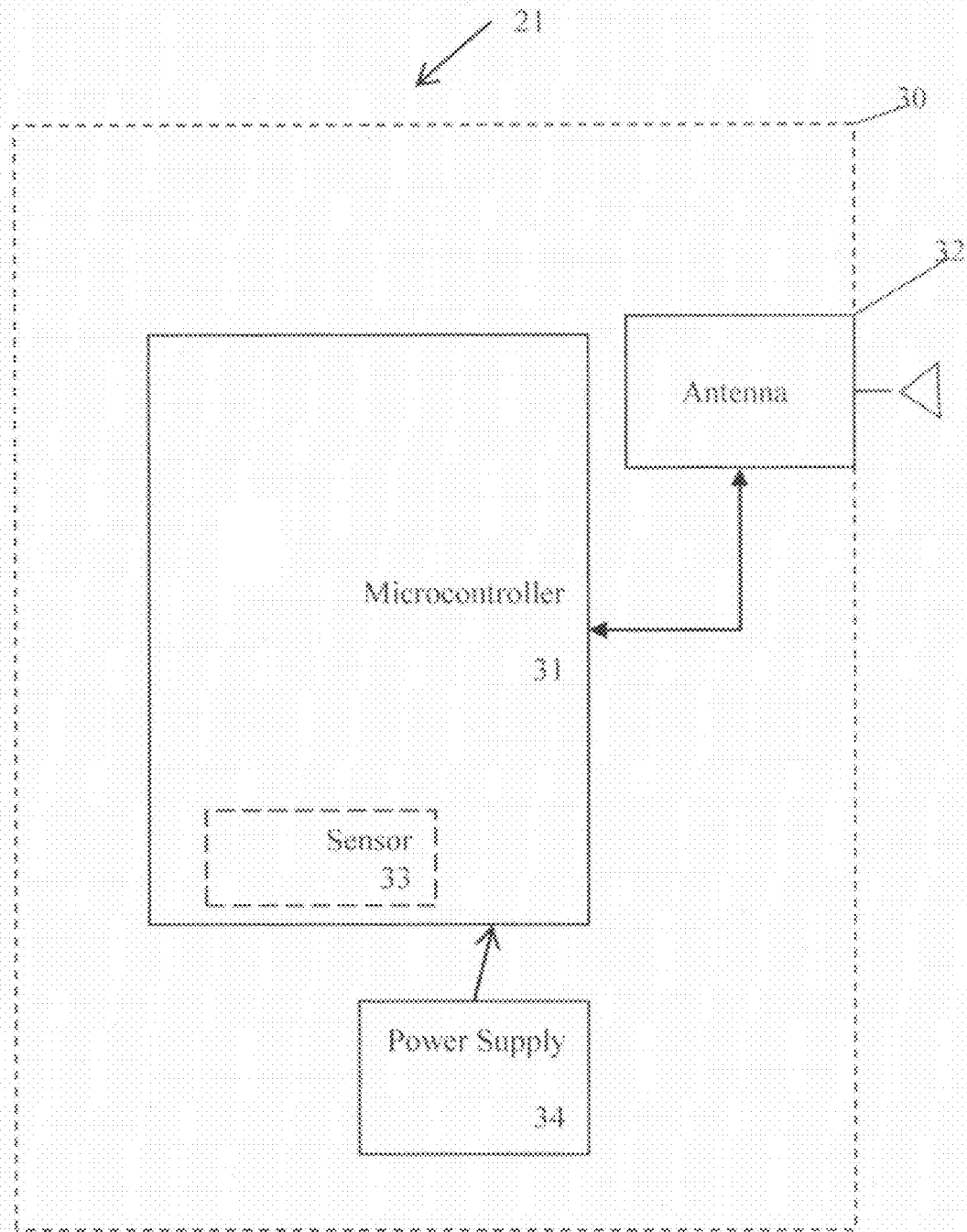
FIG. 9C is a schematic diagram of an alternative embodiment of a sensor node of the system.

FIG. 9C illustrates a wireless sub-surface sensor 21 alternatively utilized in the system 20. The wireless sub-surface sensor 21 preferably has a housing 30, a processor 31 with an integrated sensor 33, a configuration switchable antenna 32, and a power supply 34.

Figure 10:
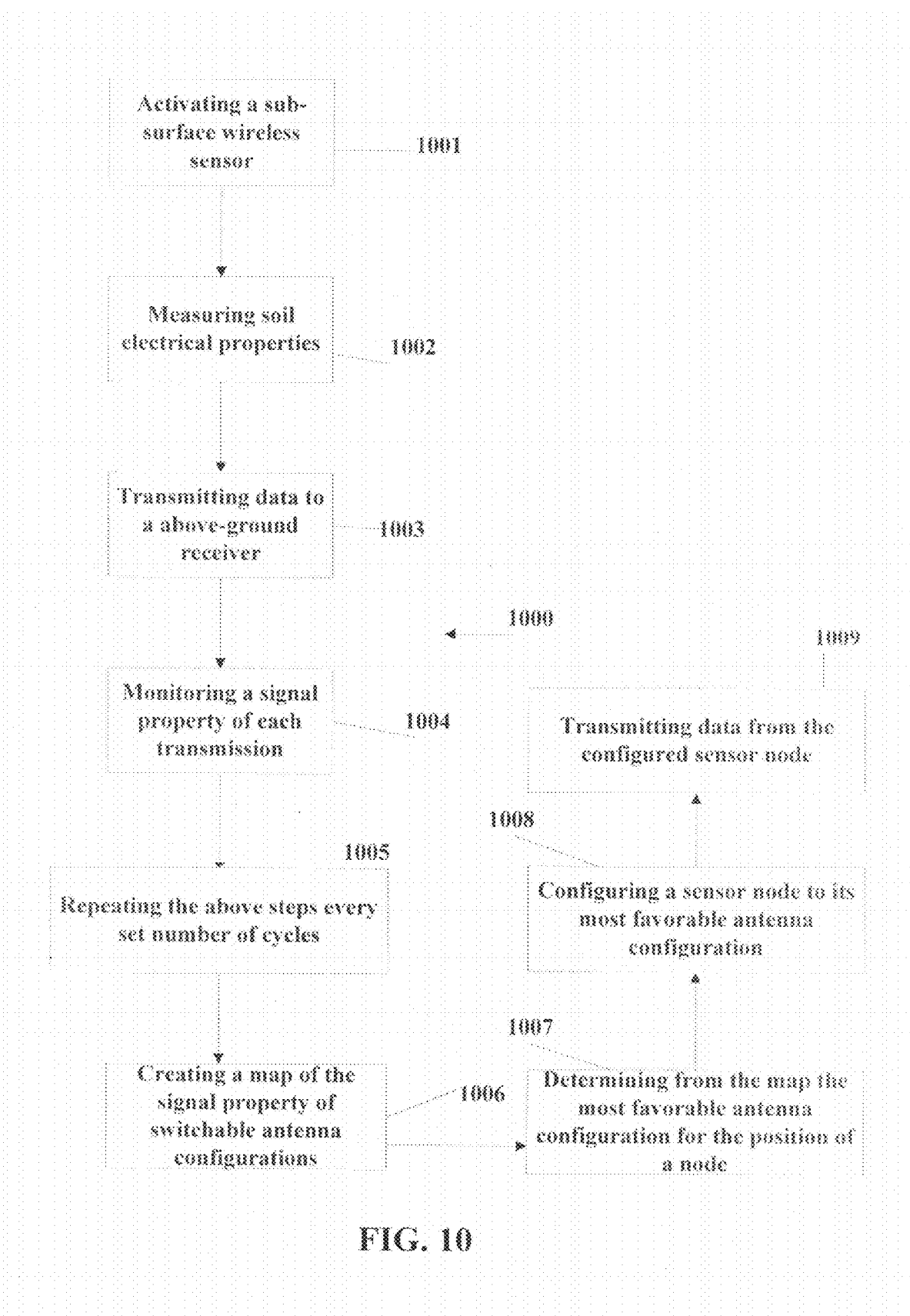
FIG. 10 is a flow chart of a preferred method for improving a communication range and communication reliability of an antenna for a wireless soil sensor buried below the surface of a land area.
Figure 11:
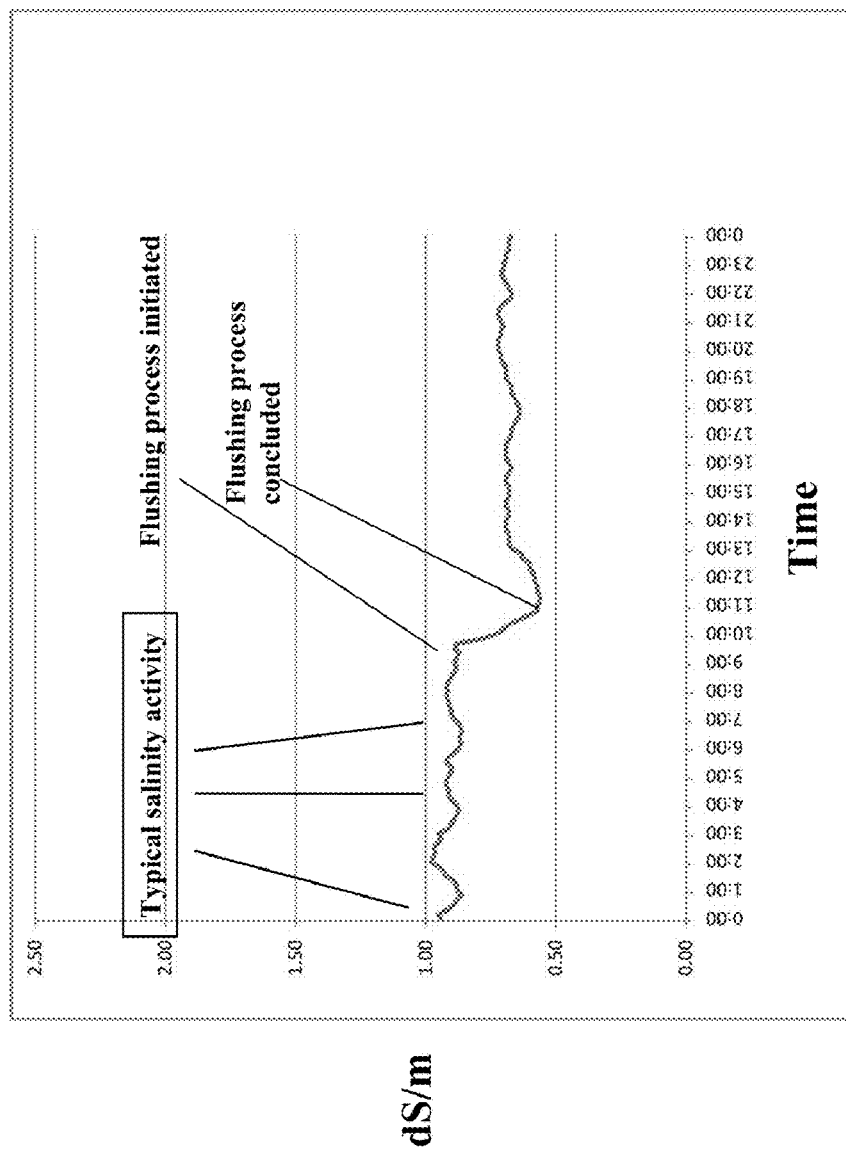
FIG. 11 is an image of flushing information.
Figure 12:
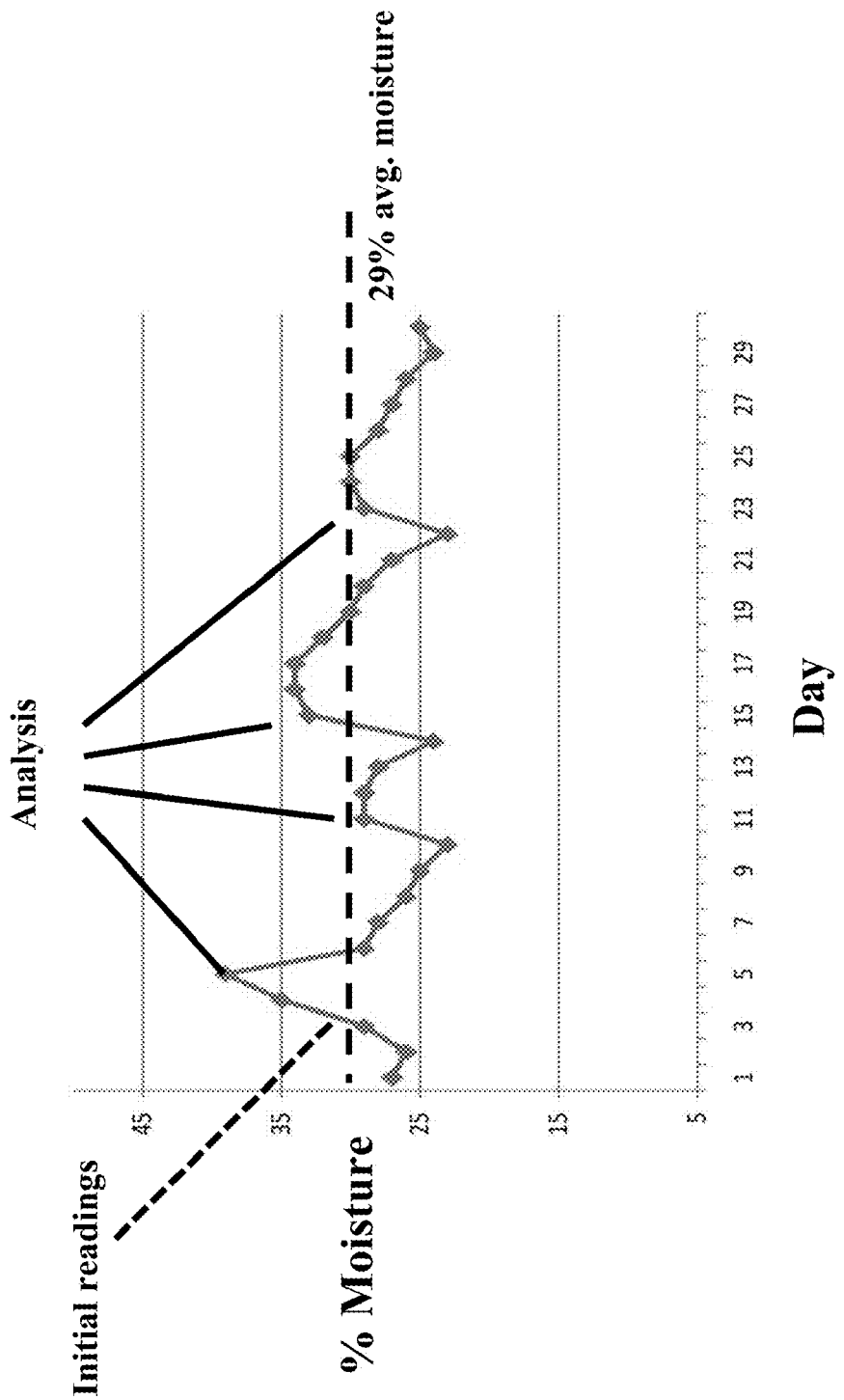
FIG. 12 is an image of indicators for the optimal zone.
Figure 13:
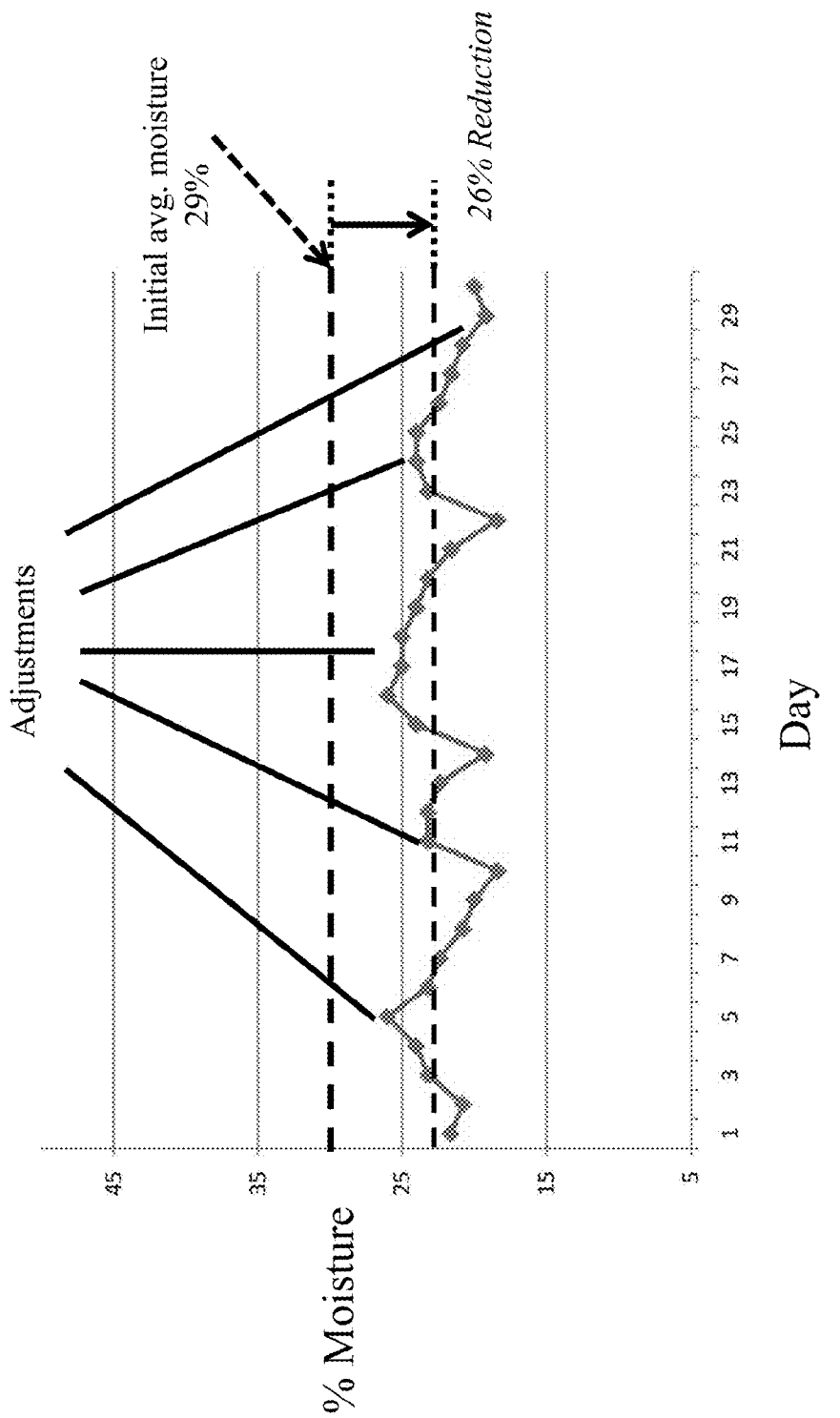
FIG. 13 is an image of proactive irrigation practices.
Figures 1, 14:
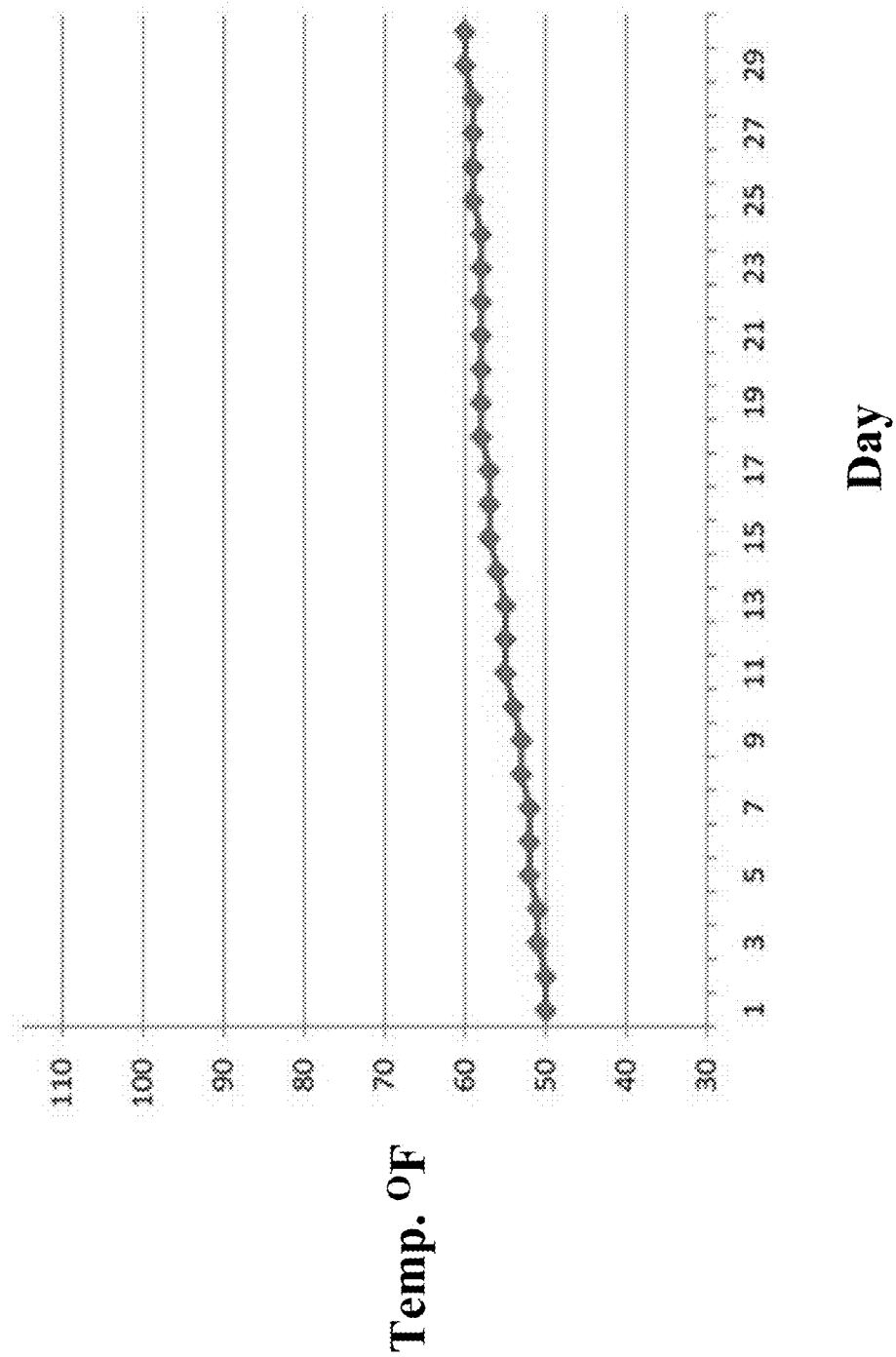
Figures 2, 14:
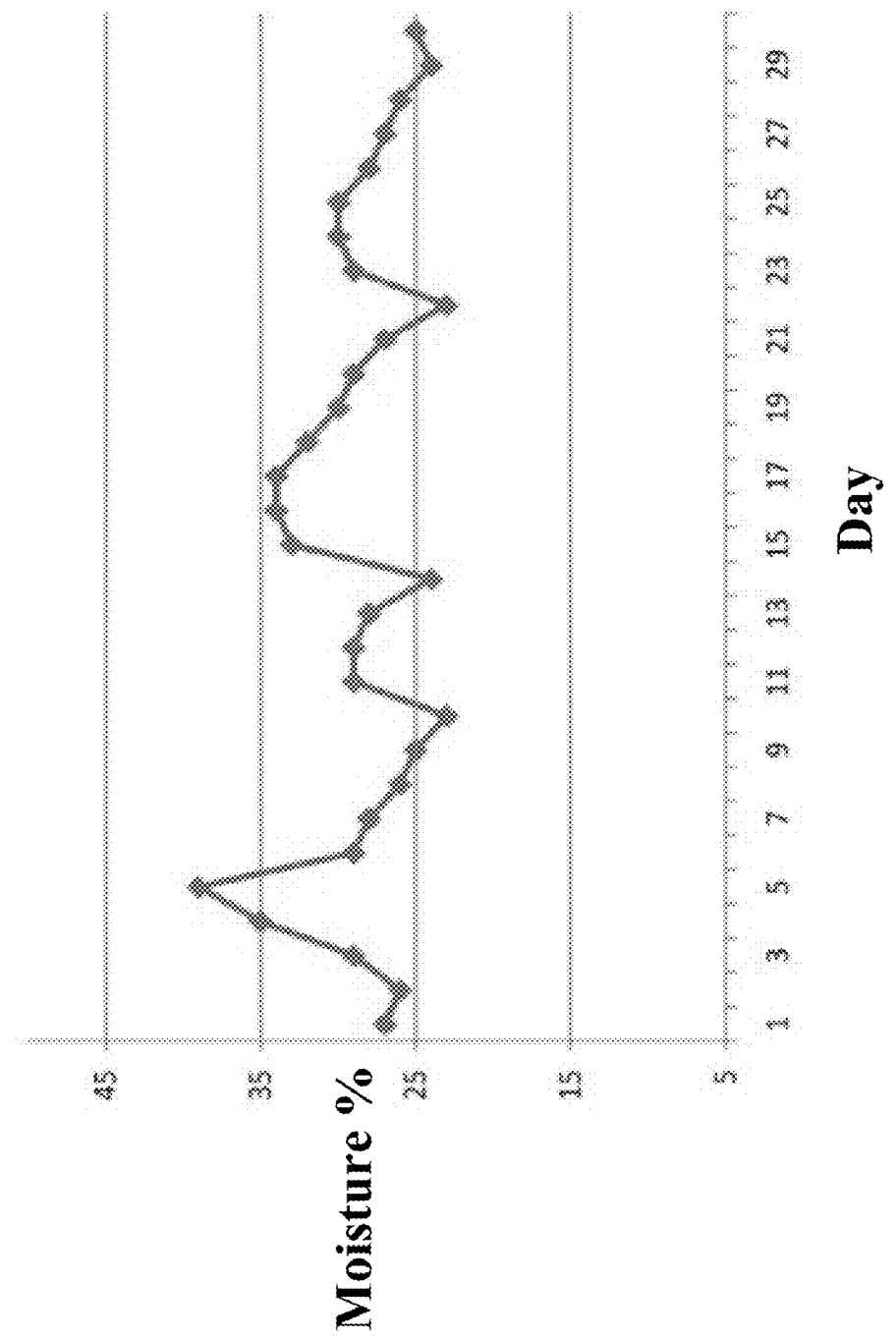
Figures 3, 14:
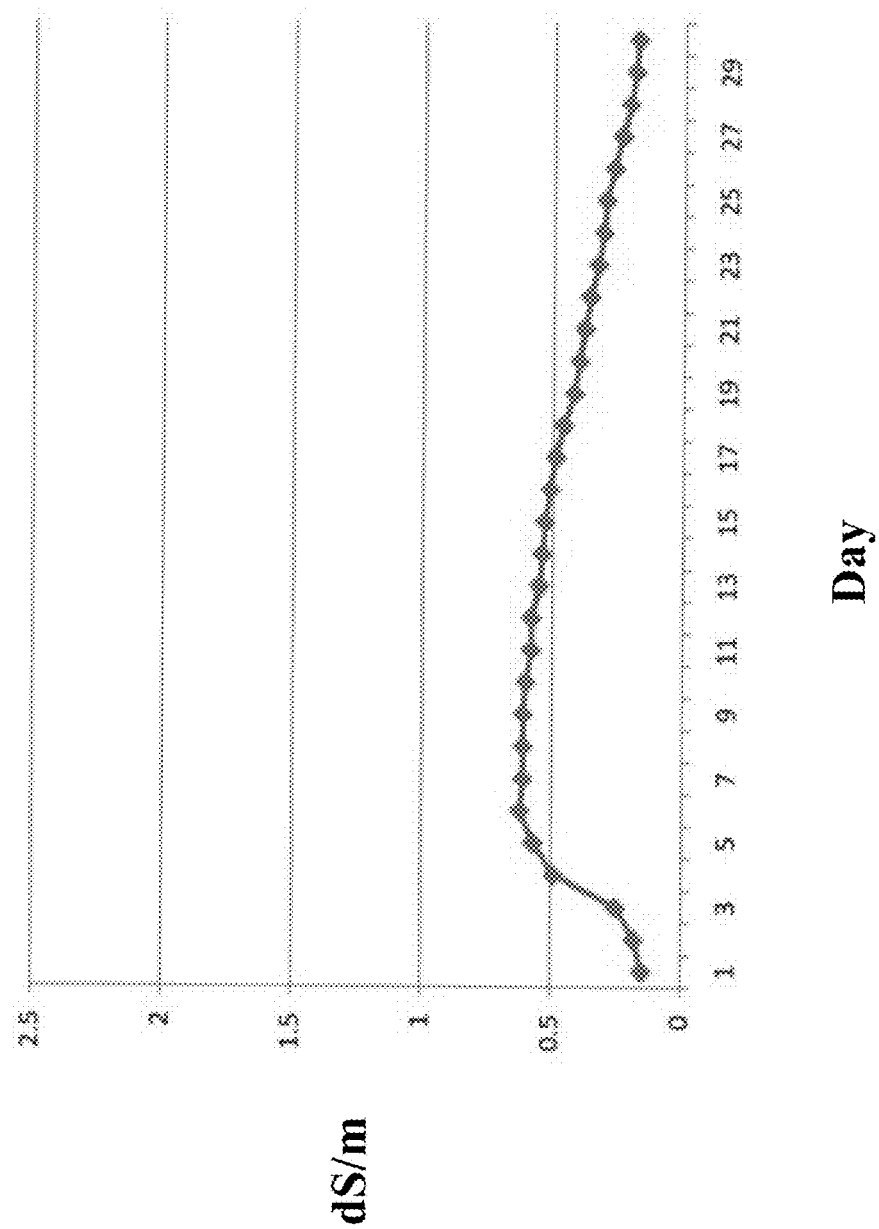
Figures 1, 14A:
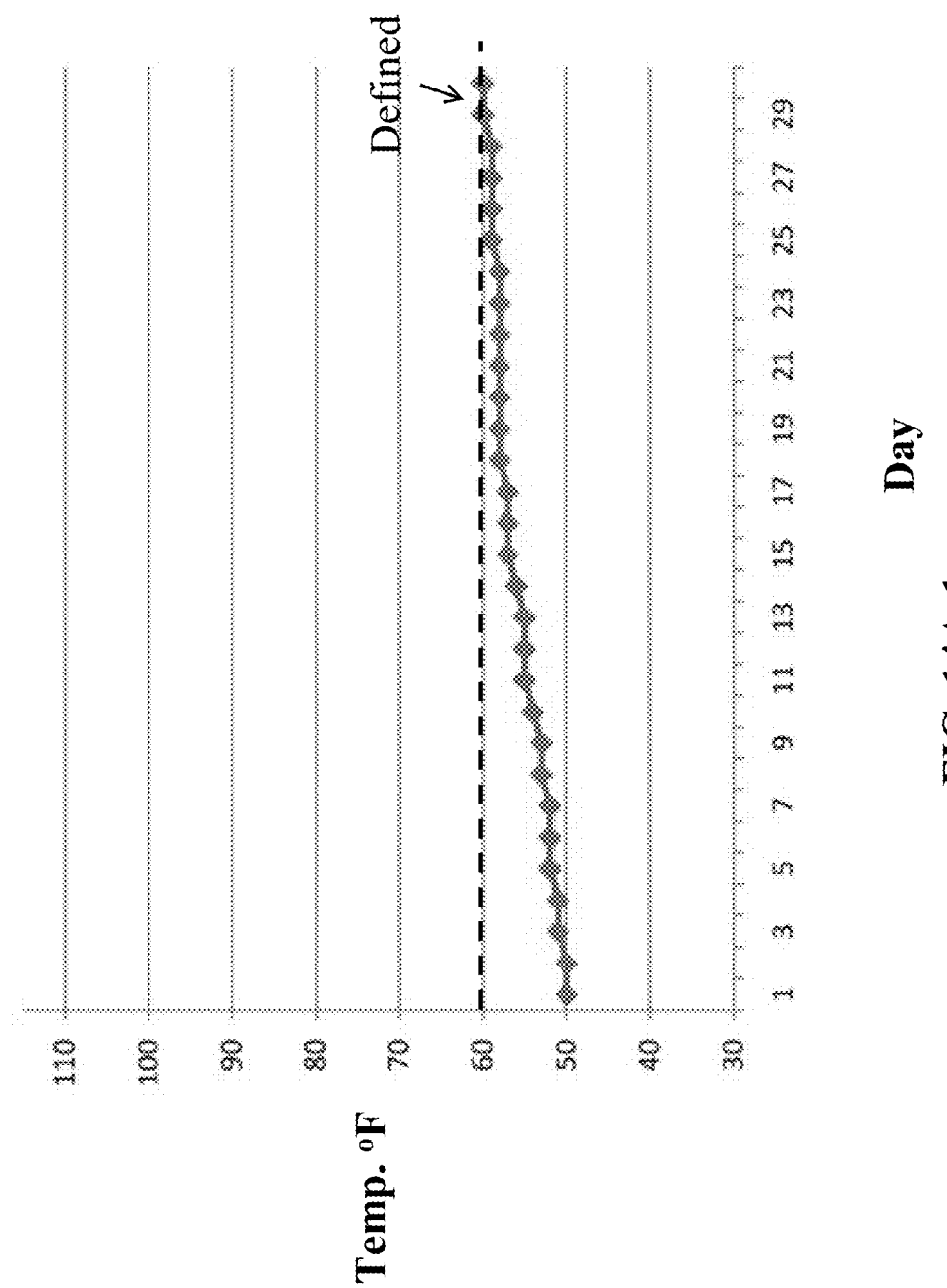
Figures 2, 14A:
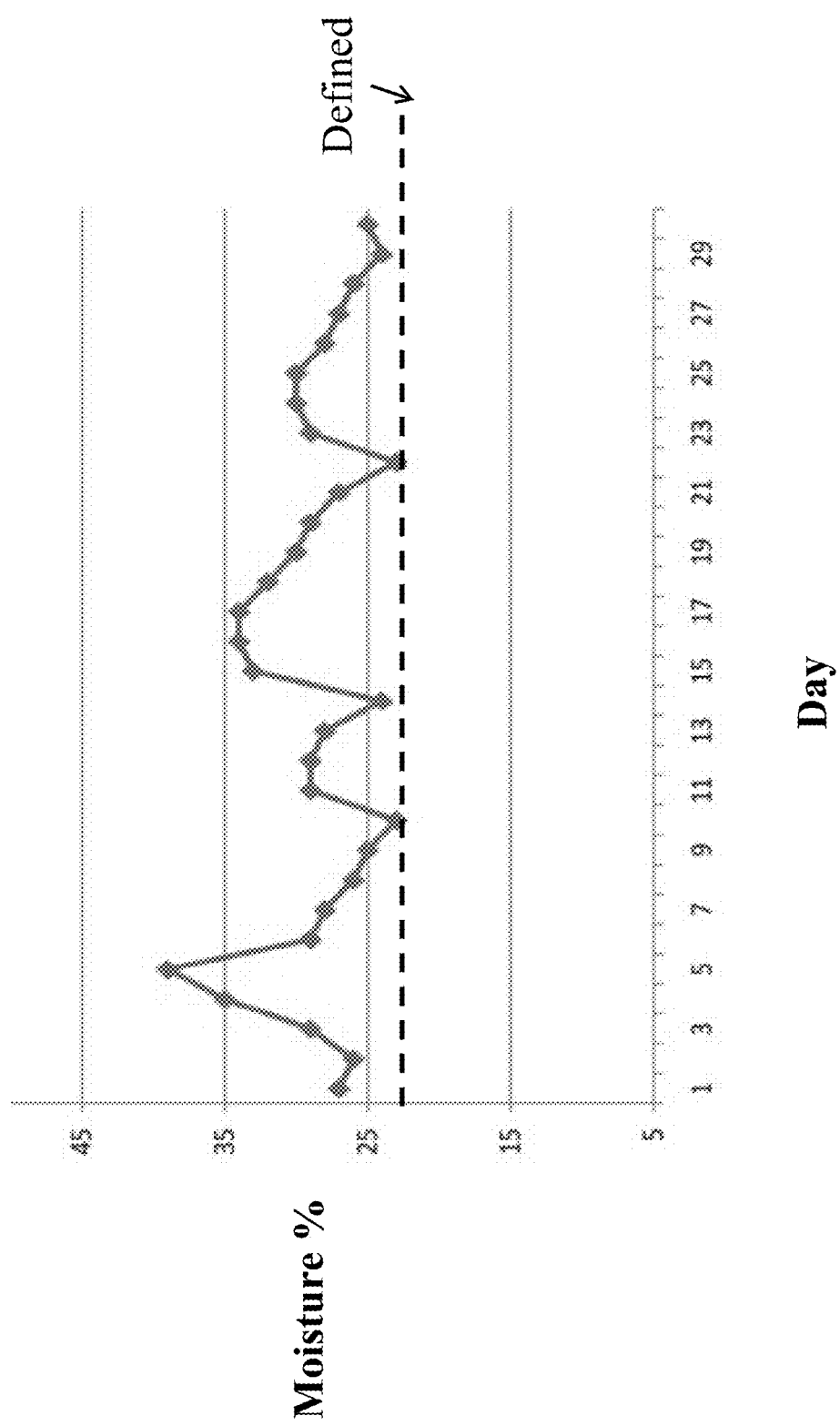
Figure 14B:
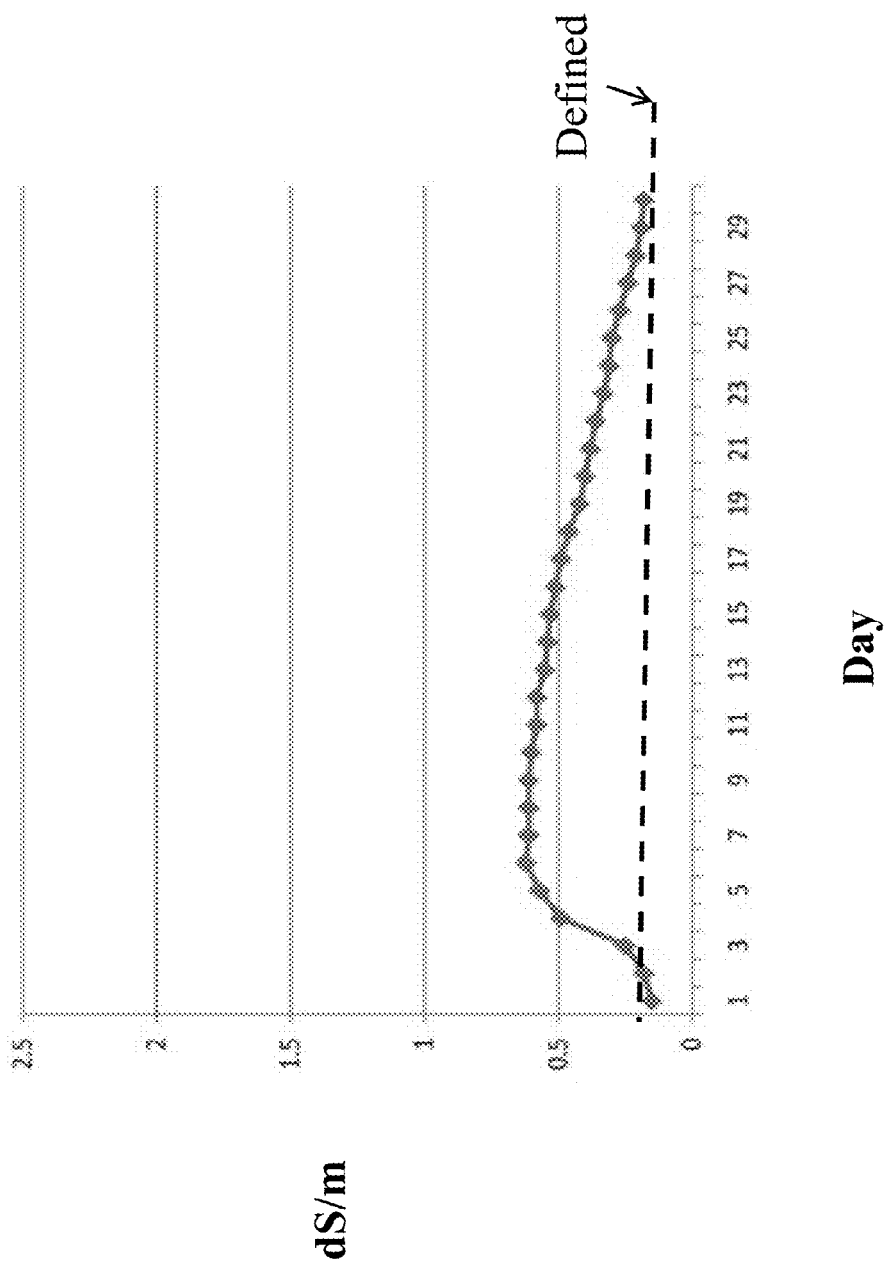
FIG. 14B is a graph of soil salinity for a number of days to demonstrate the benefit of knowing the overall conditions and defining a zone for optimum performance.
Figures 1, 14C:
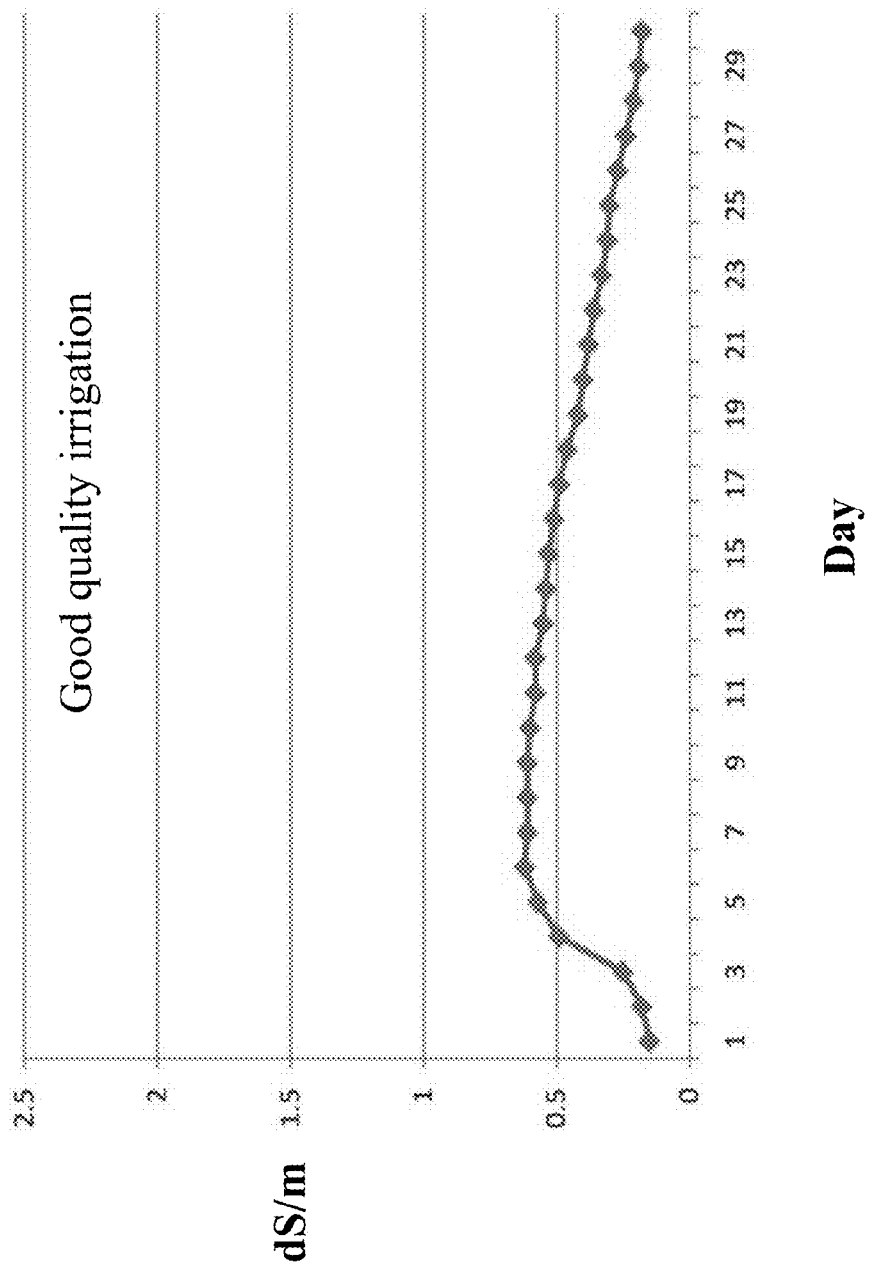
Figures 2, 14C:
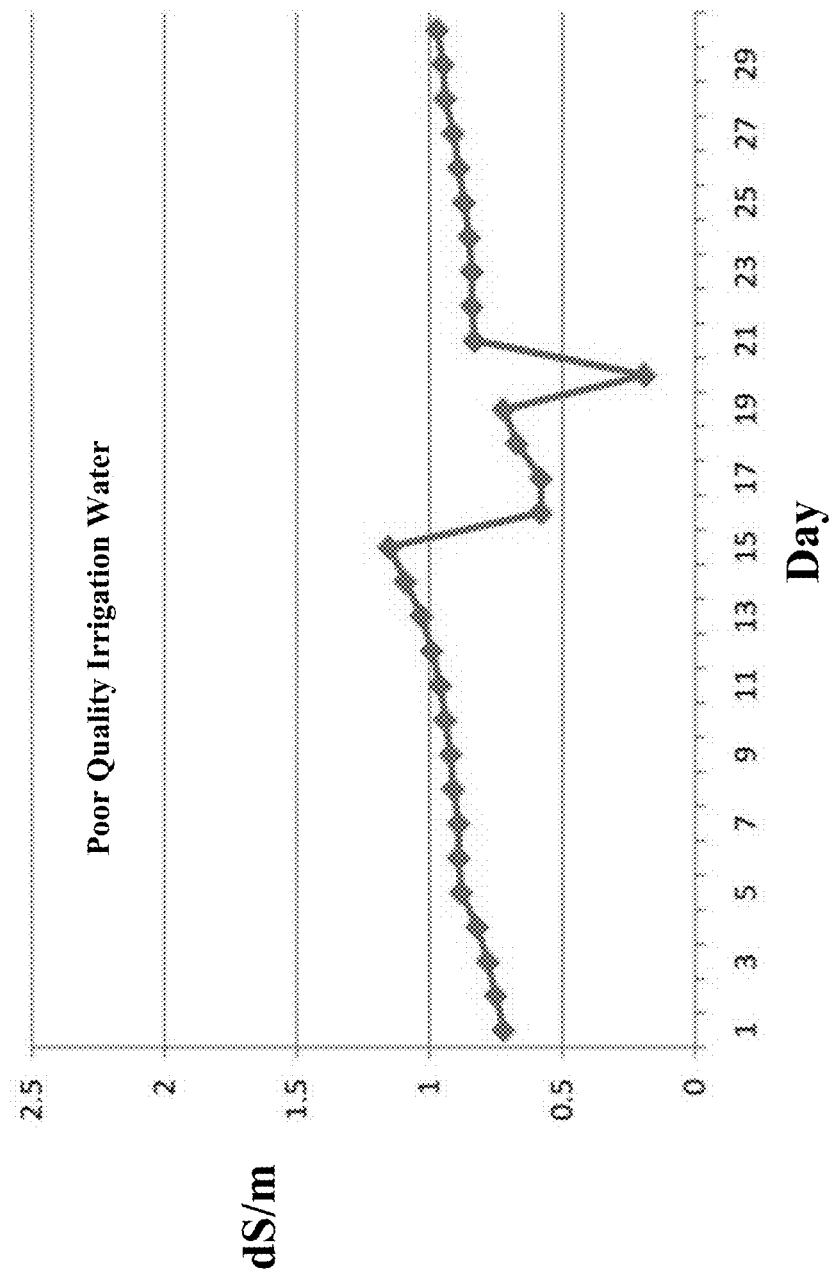

FIG. 10 is a flow chart of a preferred method 1000 for improving a communication range and communication reliability of an antenna for a wireless soil sensor buried below the surface of a land area. At block 1001, a wireless sensor is activated. At block 1002, a plurality of soil electrical properties for the land area are measured by the wireless sub-surface sensors. At block 1003, data from the wireless sensor is transmitted to at least one receiver above the surface of the land area at a plurality of switchable antenna configurations. More specifically, the wireless sub-surface sensor transmits data at a first antenna configuration, then switches to a second antenna configuration and again transmits the data to the receiver. The wireless sub-surface sensor continues to switch antenna configurations and transmit data to the receiver. At block 1004, the receiver and control engine, monitor a signal property of each transmission of data for each of the plurality of switchable antenna configurations. At block 1005, the above steps are repeated every predetermined number of sensor transmission cycle, which is preferably sixty. At block 1006, a map of the signal property for the plurality of switchable antennal configurations is created by a processor preferably located at the control engine. The map is provided to each of a plurality of wireless sub-surface sensors. At block 1007, the most favorable antenna configuration for the position of the wireless sub-surface sensor is determined from the map. At block 1008, the wireless sub-surface sensor configures the antenna to the most favorable antenna configuration. At block 1009, data from the wireless sub-surface sensor is transmitted to the receiver at the most favorable antenna configuration for that wireless sub-surface sensor.

An example of a protocol that will implement an embodiment of this approach is provided below. It is provided in the context of a two way over the air link, but can easily be applied to a one way link.

A wireless device (soil sensor 21, interrupter 12 or controller 11) typically goes through a network entry process, in which it searches for and locks onto the signals of other members of the wireless network it is entering. After the signal lock, a handshake takes place, where the entering node transmits and expects to receive a sequence of well defined messages over the air. At the conclusion of this handshake, the entering node is considered a member of the network. It will be able to transmit and receive over the air messages using a well defined protocol. It will be considered a "Joined" member. A "joined" member may maintain a connection oriented or a connection less link with its radio neighbors. (Example of a connection oriented link is a time synchronized CDMA channel between a station and a cell tower. Example of a connection-less link is the Carrier Sense Medium Access (CSMA) link between a WiFi station and its Access Point).

Typically, if the "joined" member is not able to communicate with the other end of the link within a predefined window, it loses its "joined" status, and has to go through a network entry process again. At the least, it may have to perform a less complex re-synchronization task to re-establish its time synch with the network (if is uses a connection oriented link). The link establishment, re-synch, or network entry process will continue (typically with less and less frequency, upon failed attempts) until a) the node rejoins the network, b) the time interval between reentry attempts becomes so large that the node effectively becomes dormant, or c) until the node runs out of battery.

The wireless soil sensor 21 is required to transmit messages for all of the above transactions. If the cause of loss of "joined" status is dues to surrounding soil that is too moist or too saline then the rejoin attempts will also fail. If this condition is not detected, the wireless soil sensor 21 will continue wasting scarce battery reserves for transmissions. The adaptive transmission scheduling mechanism discussed here takes into account the moisture and conductivity of the soil that surrounds the wireless soil sensor 21. It will stop transmissions until the moisture levels of the soil surrounding the node have dropped to manageable levels that will allow successful transmissions.

An example of a preferred method of adaptive transmission is as follows. A preferred method for an adaptive transmission aspect of the present invention begins with determining if (x) number of consecutive connection attempts (or transmission) have failed. Next, the method includes determining if the measured moisture level (or a composite metric that includes moisture and conductivity levels) is at some threshold (y) or above. Next, the method includes assuming the surrounding soil is too wet. Next, the method includes suspending the timers that control the transmission activity of the node. Next, the method includes, continuing to sample the moisture levels, and as long as the moisture levels are above threshold (z), attempting to connect once every predetermined time period, T (T time units only, where T is larger than typical intertransmission intervals). Next, the method includes determining when the moisture levels have dropped below a threshold (w), then un-suspending the timers and a state machine that controls transmissions. Next, the method includes, allowing the normal protocol to resume for the system.

One can manage what one can measure. And, one can do it all on a real time basis. Soil intelligence equals savings and health. The present invention is preferably a complete package of advanced software, agronomic services and wireless sensor system that helps take the guesswork out of turf management. The present invention turns raw data into useful operating thresholds that help maintain and optimize plant health and performance. The present invention provides the necessary formula that automatically alerts when and where a facility might be experiencing stress and what the treatment options are.

One aspect of the present invention has a data collection component of the software, which allows for monitoring in real time, from an office or from on-site or remote locations, the key variables of moisture, salinity and temperature from each sensor site. The graphic displays are user-friendly and the present invention helps set high-low threshold ranges for each sensor location so that one instantly knows whether the soil is in or out of the optimal range for growth conditions and playability. By continuously analyzing the recorded data and thresholds for each location, this component visually alerts one to conditions at each sensor location and suggests what actions are needed to be more efficient and effective.

One aspect of the present invention optimizes turf and crop health and playability by measuring root zone moisture, salinity and temperature and applying best practices to your turf management. Once the wireless soil sensors 21 are in the ground sending raw data, an optimal zone is devised by analyzing accumulated sensor data, putting decades of agronomic experience to use and applying tested scientific principles. The Zone defines the upper and lower operating thresholds to ensure plant health. This helps with: course evaluation; soil and water analyses; review of existing practices including irrigation, nutritional inputs and maintenance; threshold determinations; sensor placement and more. On a real-time basis, one can manage greens, tees, fairways and rough to keep a facility in prime condition.

The wireless soil sensor 21 provides wireless interface between the sensing elements and the Communication Control Nodes (CCNs) that preferably form a mesh network. The key features include the shape: 8×4 inches. Buried with a Standard Cup Cutter. Supports sensors: analog or digital. 3 "D" Cell batteries: 4+ years life, field replaceable. 1 Watt FHSS radio board supports approximately 400 ft. range 4 in. in ground. Sensor interface and antenna for over air programming for product upgrades.

The key functionalities of the wireless soil sensor 21 are as follows: provide accurate, real-time data on soil moisture, temperature and salinity. Key Features: Pre calibrated for sand, silt and clay. Moisture measurement. Accuracy: +/−0.02 WFV from 0 to saturation at <2.5 dS/m conductivity. +/−0.04 WFV from 0 to saturation at 2.5-5 dS/m conductivity. Repeatability: +/−0.001 WFV. WFV is the fraction of soil occupied by water, a soil at 10% soil moisture has a WFV of 0.10. Conductivity measurement: Accuracy: +/−2% or 0.02 dS/m, whichever is greater, 0-2.5 dS/m. +/−5%, 2.5-5 dS/m. Repeatability: +/−1% or 0.01 dS/m whichever is greater, 0-2.5 dS/m. +/−4%, 2.5-5 dS/m. Temperature measurement: Accuracy: +/−0.5° C. from −10 to +50° C., +/−1° F. from 14 to 122° F. Repeatability: 0.05° C., 0.1° F. Benefits: Dual sensors allow gradients of soil moisture, conductivity, and temperature to be monitored. High accuracy and repeatability. No individual sensor calibration required.

Above-Ground Wireless Mesh Network: Communication Control Nodes. Key Functionality: CCNs are the interface to the Sensor Nodes. Each is a radio node that automatically joins and forms the mesh network on power up. Key Features: Range of ~1 mile above ground unobstructed. Requires 1 Amp while transmitting. 12-24 Volt AC or DC power. Can be attached via 110/220 Volt power adapter. Weather proof enclosure. Benefits: Self forming, self healing, multihop mesh network; No special wiring required; Two way communications with link quality statistics; Control of buried nodes; The multihop mesh allows extension of the wireless coverage area far beyond the nominal range of the radios.

Agronomy. Soil health impacts everything grown above. What is agronomy? It is the study of plant and soil sciences and how they impact crop and plant production, performance and yield. Every plant has specific tolerances to environmental variables like moisture, temperature and salinity which impact the ability to grow, flourish, proliferate and perform to expectations. Agronomists using the present invention help define those optimal threshold levels as well as their impacts on root, leaf and lateral growth, responses to man-made or natural environmental stress, and resistance to disease and insect pressure. As a result, in this case water usage was reduced by nearly 30% while playability was enhanced uniformly. The indicator of the present invention predicts the likelihood for disease outbreaks before they happen.

The software package utilized feeds off data provided by the wireless soil sensors 21 and wireless communications system. It displays real time conditions and provides comprehensive intelligence and predictive actions. The system helps establish health- and performance-optimizing operating threshold ranges, evaluate your data and current practices, and refine existing programs. The results, optimal turf conditions and real savings, will generate a strong and lasting return on investment. The agronomic benefits include more efficient salinity management, uniform irrigation, deeper rooting, predictive disease control and healthier, more stable conditions. There are environmental benefits as well like water conservation, reduced use of phosphates, nitrates and pesticides, a reduced carbon/water footprint and regulatory compliance.

Real time sensor measurements using the present invention also include soil oxygen, pH, concentrations of specific ion species—($Na+$ has a very detrimental effect compared to the same concentration of $Ca+2$). Pollutant measurements include both hydrocarbons (oils, gasoline, etc.) and metals (chromium, lead, etc.).

As to the wireless transmission network, an alternative process of an adaptive model may be utilized with the present invention. An antenna, designed for efficient RF communication in air is relatively straightforward because the key electrical properties of the transmission medium (air) are well known and essentially constant. In below ground RF transmission, the key properties of the soils vary greatly with moisture content and salinity hence it is a much more difficult problem to design an efficient antenna. In addition, the best antenna design is influenced by how deeply buried the antenna is. The present invention includes elements to the antenna circuit that, under control of microcontroller, allow for varying the properties of the antenna to more closely match the conditions and improve range and reliability of communication. The wireless sub-surface sensor 21 measures both the dielectric constant of the soil (moisture) and conductivity (salinity) directly. Hence, the sensor measures precisely the two most important factors affecting antenna efficiency.

In a predictive model, the method includes activating a sensor and measuring soil electrical properties. The method also includes, based on the soil properties, activating antenna elements to give an effective transmission. The method also includes transmitting sensor data.

In an adaptive model, the method includes activating a sensor and measuring soil electrical properties. The method also includes transmitting data repeatedly until all switchable antenna configurations have been attempted. The method also includes monitoring signal strength for each transmission. The method also includes repeat this process possibly every 60 sensor transmissions.

As time progress, a receiver can put together a two dimensional map (soil dielectric constant on one axis, soil conductivity on the other) with received power for all antenna configurations. The map is downloaded on some regular schedule to the buried sensor node. When the wireless sub-surface sensor 21 makes a measurement, the sensor reviews the map for the antenna configuration that gives the highest received signal power at the receiver for the current conditions. A node configures an antenna and sends a packet of data. Even after the map is downloaded, every 60 sensor readings preferably have all of the different antenna configurations attempted which allows the map to evolve.

The advantage of this adaptive process is that it can make an allowance for the actual depth of burial as well as the relative antenna locations and orientations. This is important because different antenna configurations have different radiation patterns. Hence, it is possible that a less than ideal antenna configuration works best in that it has the highest radiated power in the particular direction and polarization that the receiver antenna lies in.

Figure 15:
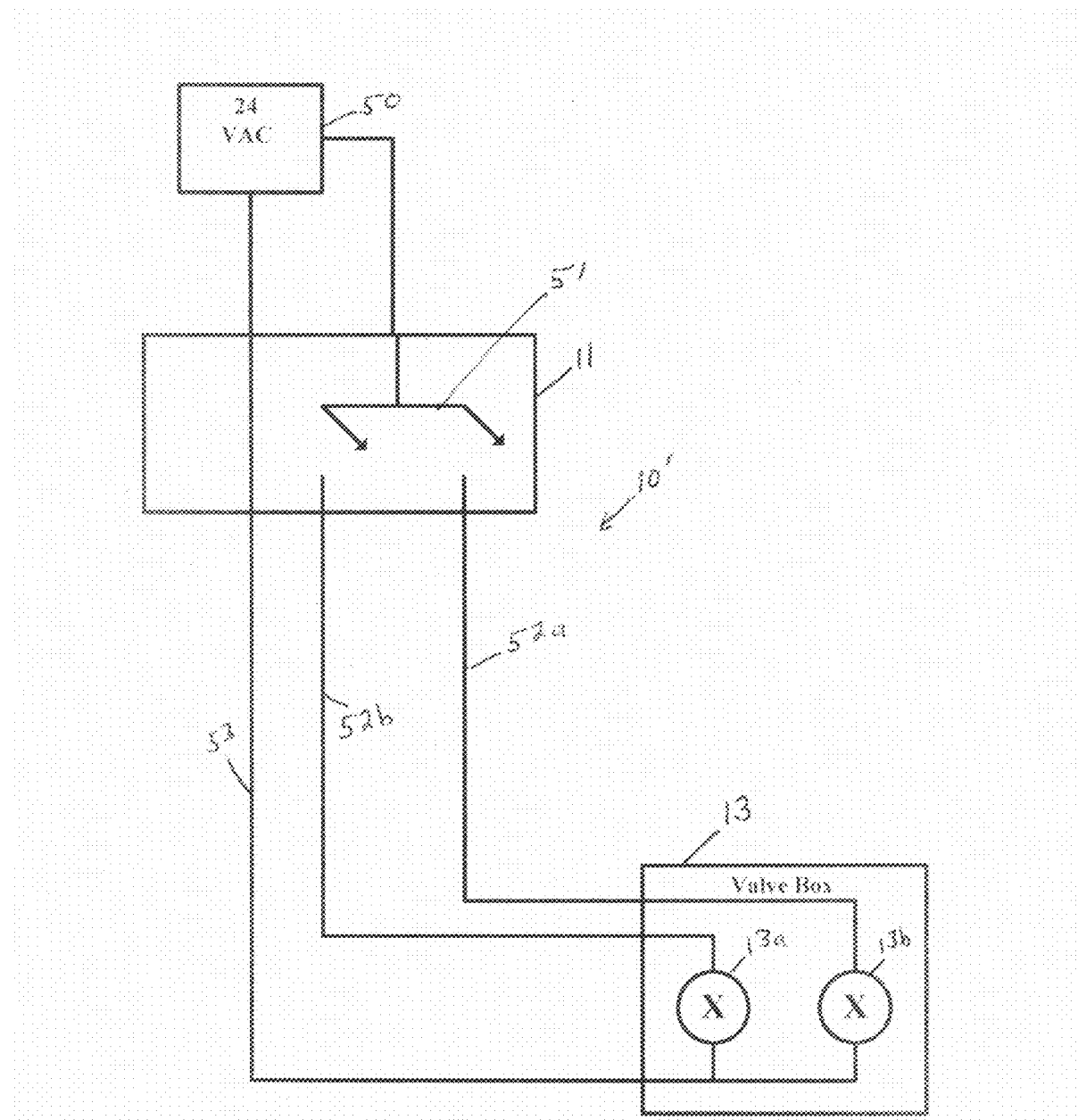
FIG. 15 is a schematic diagram of a prior art irrigation control system.
Figure 18:
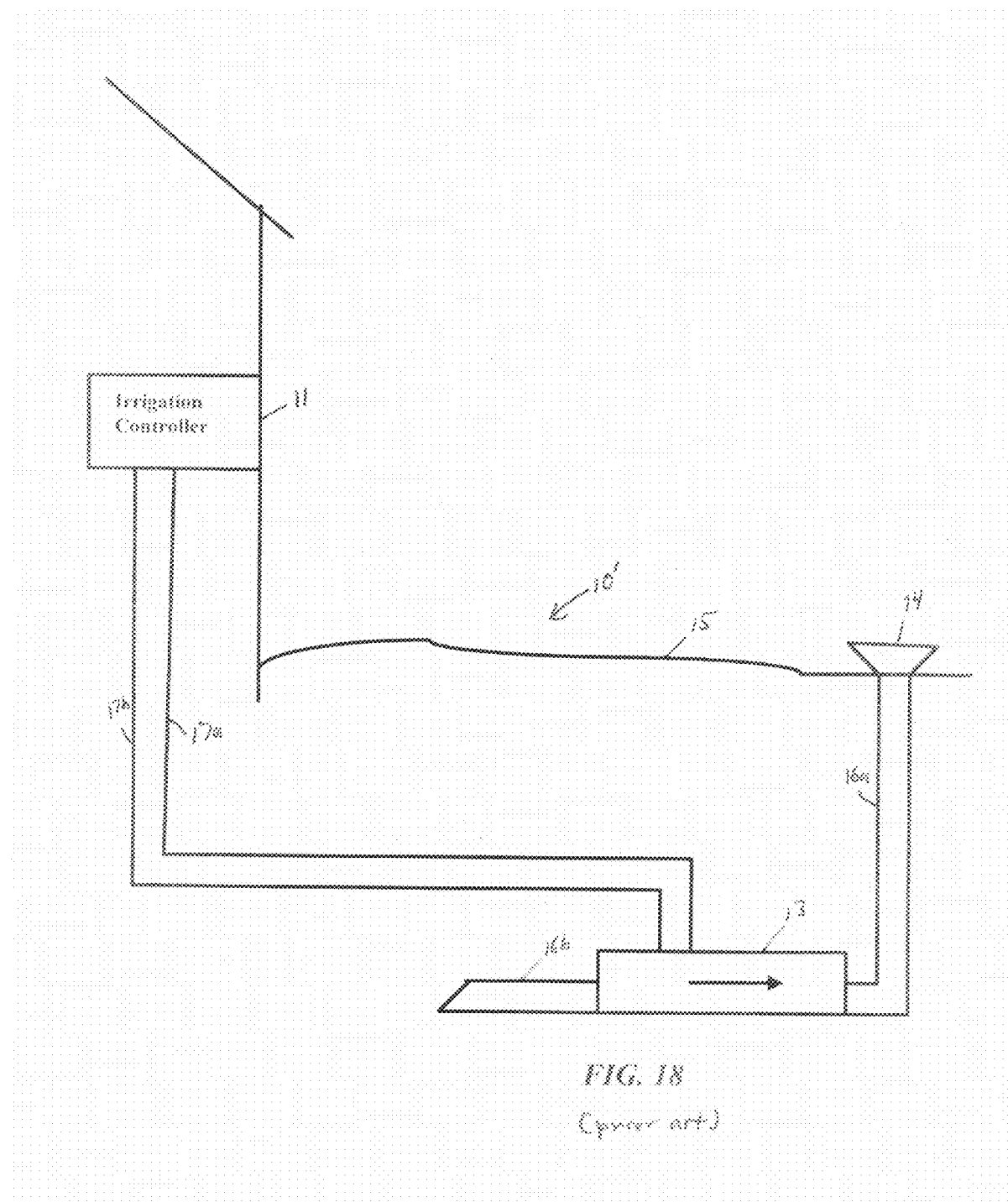
FIG. 18 is a schematic diagram of a prior art irrigation control system.

As shown in FIG. 15, an irrigation system 10' includes a 24 VAC power supply, a controller 11, and a valve box 13 with valves 123a and 13b. These irrigation systems 10' work by using a 24 volt alternating current source to open valves 13a and 13b. When no current flows (open switch 51), the valves 13a and 13b are closed and no water flows. A controller/timer 11 is used to turn on the current to the separate valves 13a and 13b. Usually there is a "common" wire 53 that returns the current from all valves 13a and 13b. Separate "hot" wires 52a and 52b are used for each of the valves 13a and 13b. As shown in FIG. 18, the irrigation controller 11 controls the valve box 13 through wires 17a and 17b to provide water form source pipe 16b to sprinkler pipe 16a for dispersion on a soil 15 through sprinkler 14.

Figure 19:
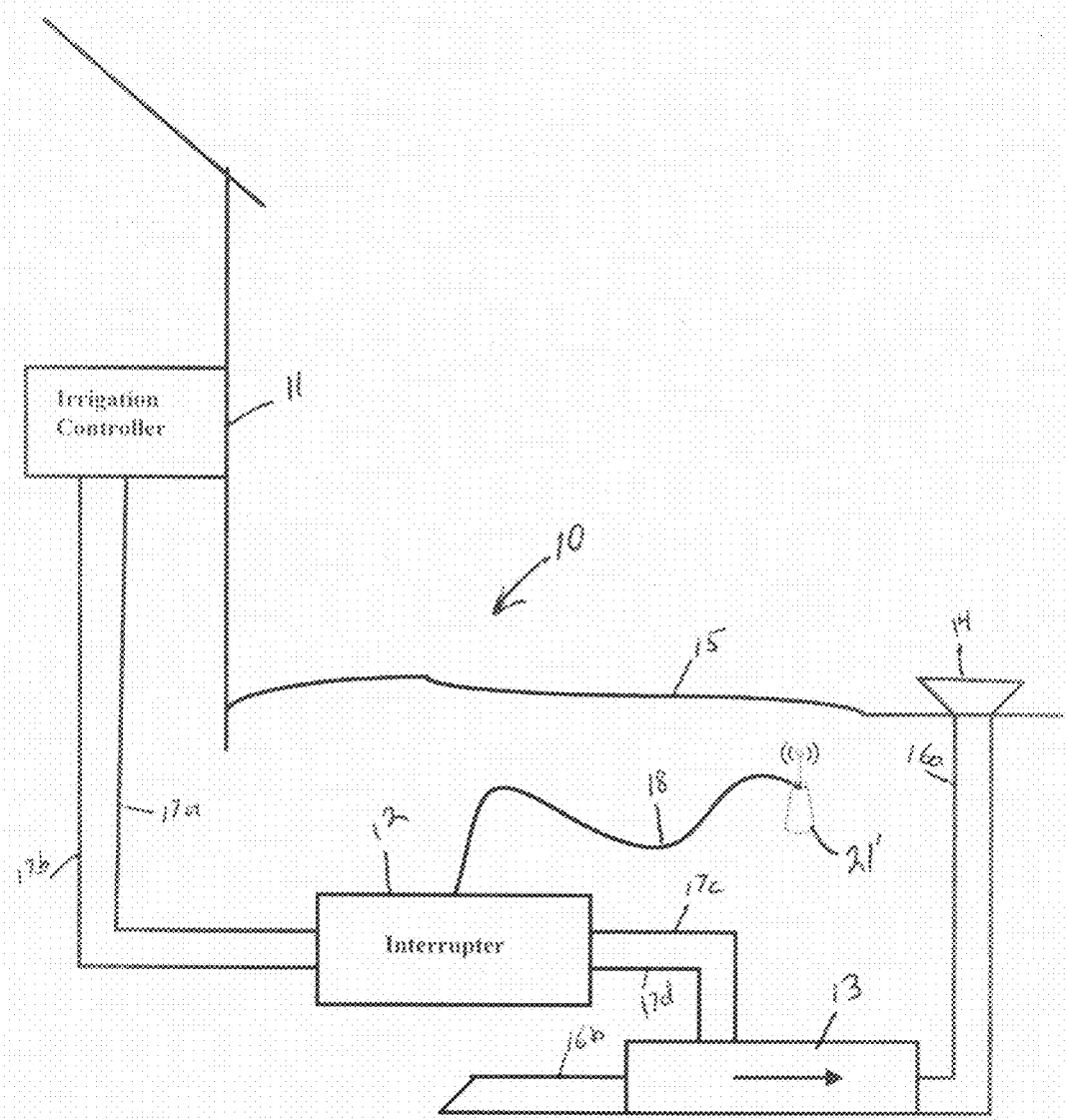
FIG. 19 is a schematic diagram of an irrigation control system with a tethered sensor.

As shown in FIG. 19, the prior art is improved upon by a system 10 with a tethered sensor 21' in which is a sensor coupled to an interrupter 12 wired into the wirings 17a, 17b, 17c and 17d of the valve box 13. The interrupter 12 acts to turn off a scheduled irrigation if the moisture exceeds a predetermined threshold established by a user. The interrupter 12 acts as an in-line switch that closes (allowing current to flow and the valve 13 to open) only if the controller 11 starts a scheduled irrigation and the soil moisture is below a predetermined threshold established by a user). In the system 10 of FIG. 19, the interrupter 12 can only interrupt a scheduled irrigation, not initiate an irrigation. The system 10 has a sensor 21 which is cabled (no wireless communication). The system 10 of FIG. 19 has the advantage of being very simple, it is capable of being easily installed into virtually all existing irrigation systems, and it requires no independent power (the system 10 draws power off the 24 VAC irrigation line).

Figure 20:
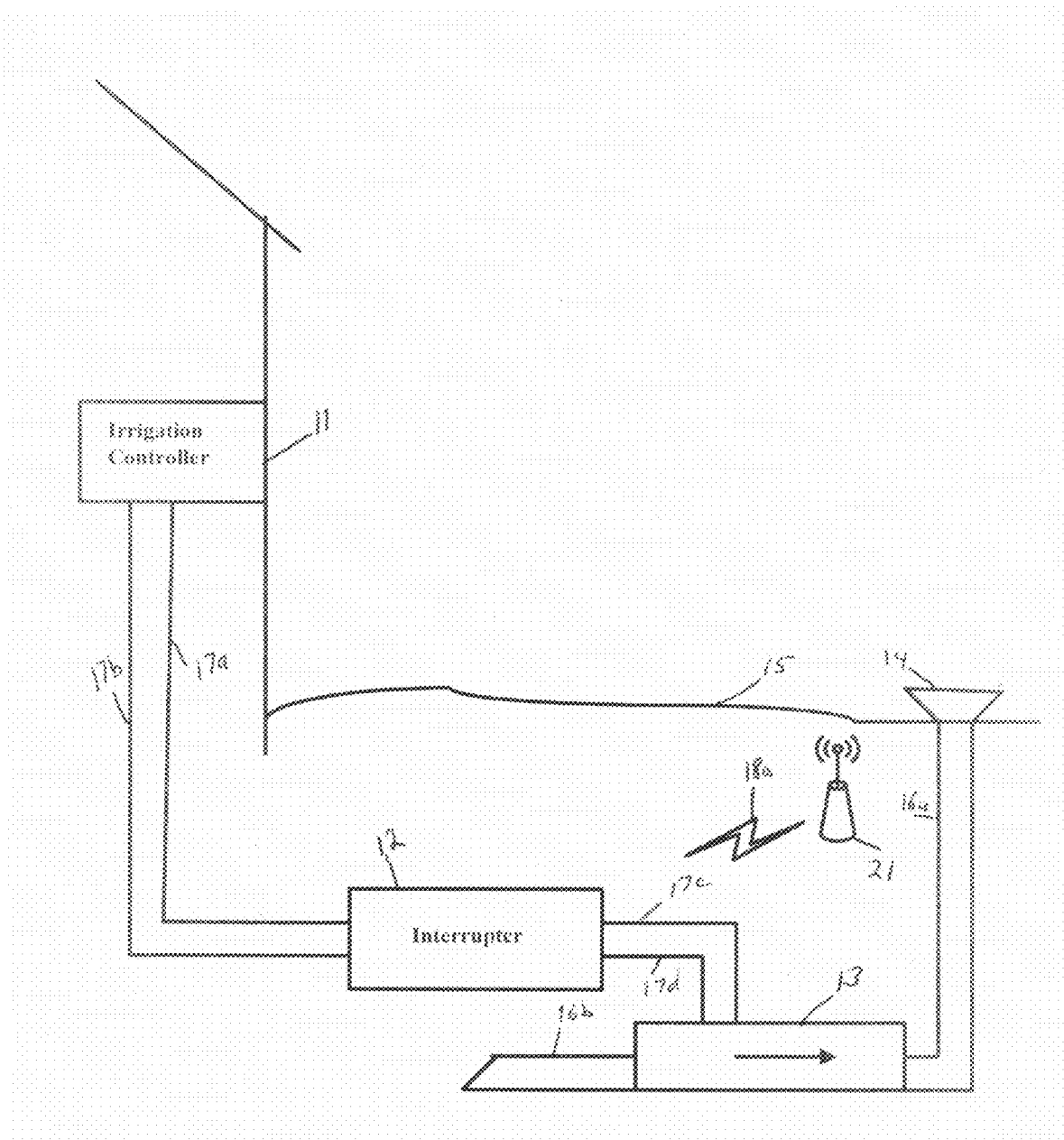
FIG. 20 is a schematic diagram of an irrigation control system with a wireless interrupt.

As shown in FIG. 20, a wireless interrupt approach is similar to the "Tethered Sensor" system 10 of FIG. 19, except that wireless communication is used between a wireless soil sensor 21 and an interrupter 12. The wireless soil sensor 21 requires battery power and the interrupter 12 requires a battery to accommodate flexible wireless reporting. The principle advantage of the system 10 of FIG. 20 is that no cabling is needed, and installation is simpler than the tethered system 10 of FIG. 19. As shown in FIG. 20, the wireless soil sensor 21 transmits a wireless signal 18a to the interrupter 12 pertaining to the moisture levels of the soil in a particular soil area.

Figure 21:
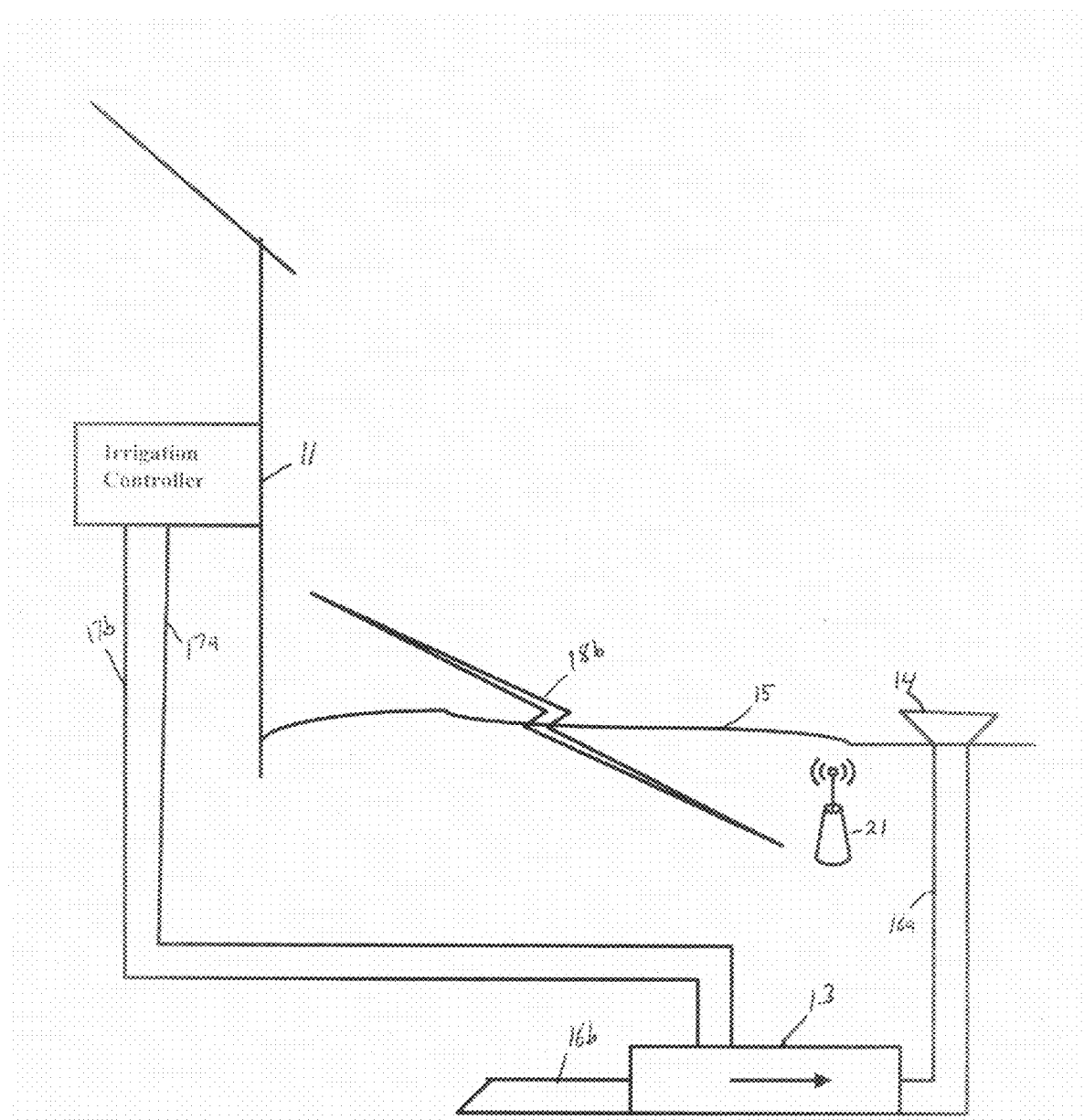
FIG. 21 is a schematic diagram of an irrigation control system with a wireless controller.

A wireless controller system 10 is shown in FIG. 21. The wireless controller system 10 uses a wireless link back to a wireless irrigation controller 11 (there is no "interrupter") The principle advantage of the wireless controller system 10 of FIG. 21 is that the wireless soil sensors 21 preferably initiate irrigation if needed (allowing for the user to set scheduled irrigation times as well if desired). A user also may allow the wireless controller 11 to look at more than one wireless soil sensor 21 for each irrigation zone (area irrigated by one valve 13) taking an average, use the lowest value, etc. One can also allow for simpler level adjusting, including such features as a "hot day" button nudging the target water levels up a notch and many others.

The goal of one aspect of the present invention is to develop an inexpensive and easy to install system compatible with existing irrigation systems that can be quickly configured by homeowners/landscapers of limited technical sophistication. An objective of the present invention is an overall lower cost, a system that is easy to install in existing and new irrigation systems, setup that is as easy to use as a traditional irrigation controller, and careful design of setup features, default modes, user input device and display to give a superior customer interface.

Irrigation interrupt of the system interfaces simply with existing irrigation control systems to over-ride scheduled irrigation when moisture levels hit user settable thresholds. When operating in this manner, the system is incapable of initiating an irrigation event and needs to be used with a conventional irrigation controller. An irrigation controller 11 of the system 10 can initiate and stop irrigation events and replaces existing installation irrigation controllers or is suitable for complete control of new installations through both timing of irrigation to certain times of the day as well as based on near real-time soil moisture data.

As mentioned above, a typical irrigation controller system 10' is shown in FIG. 15. The system 10' includes a 24 VAC power supply connected to 120 VAC and an irrigation controller 11. Wiring 52a and 52b leads from the controller 11 to one or more valve boxes 13. When the current loop is closed, the valves 13a and 13b open and a zone is watered. Typically, the controller 11 is set to turn on and off valves at predetermined times for a set time.

Figure 16:
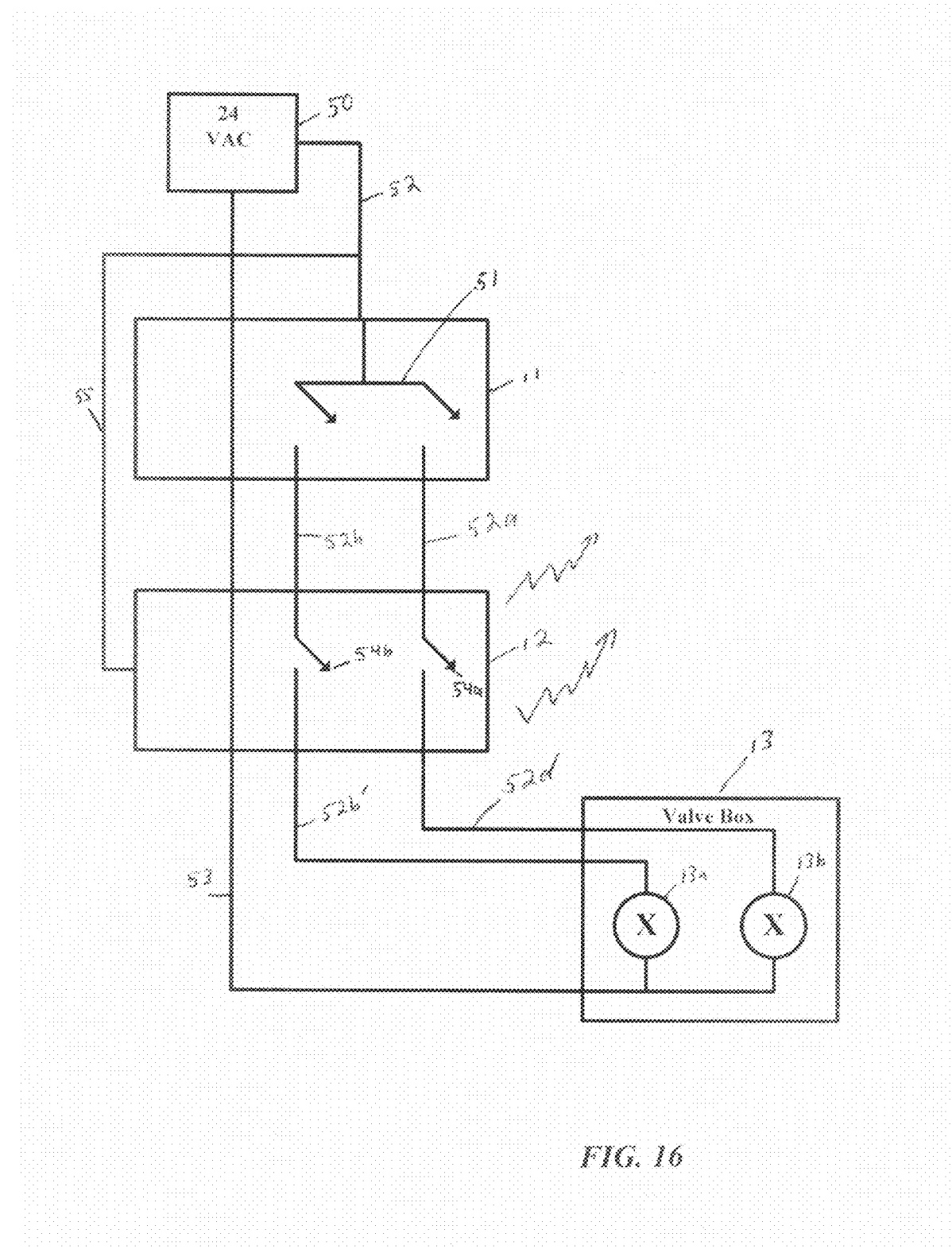
FIG. 16 is a schematic diagram of an irrigation control system with an irrigation interrupt.

In the irrigation interrupt system 10, as shown in FIG. 16, the interrupter 12 is positioned between the standard irrigation controller 11 and the valves 13a and 13b. A wireless soil sensor 21 is placed in each irrigation zone and the wireless soil sensor 21 is in periodic communication with the irrigation controller 12. In this system, watering only occurs when both the standard irrigation controller 11 indicates that it is time to water and the irrigation interrupter 12 indicates that soil moisture is below a predetermined threshold. The interrupter 12 opens switch 54a and 54b to terminate the current flow through lines 52a' and 52b' and close the valves 13a and 13b. Line 55 provides power to the interrupter 12, especially when the switch 51 of the controller 11 is open.

Figure 17:
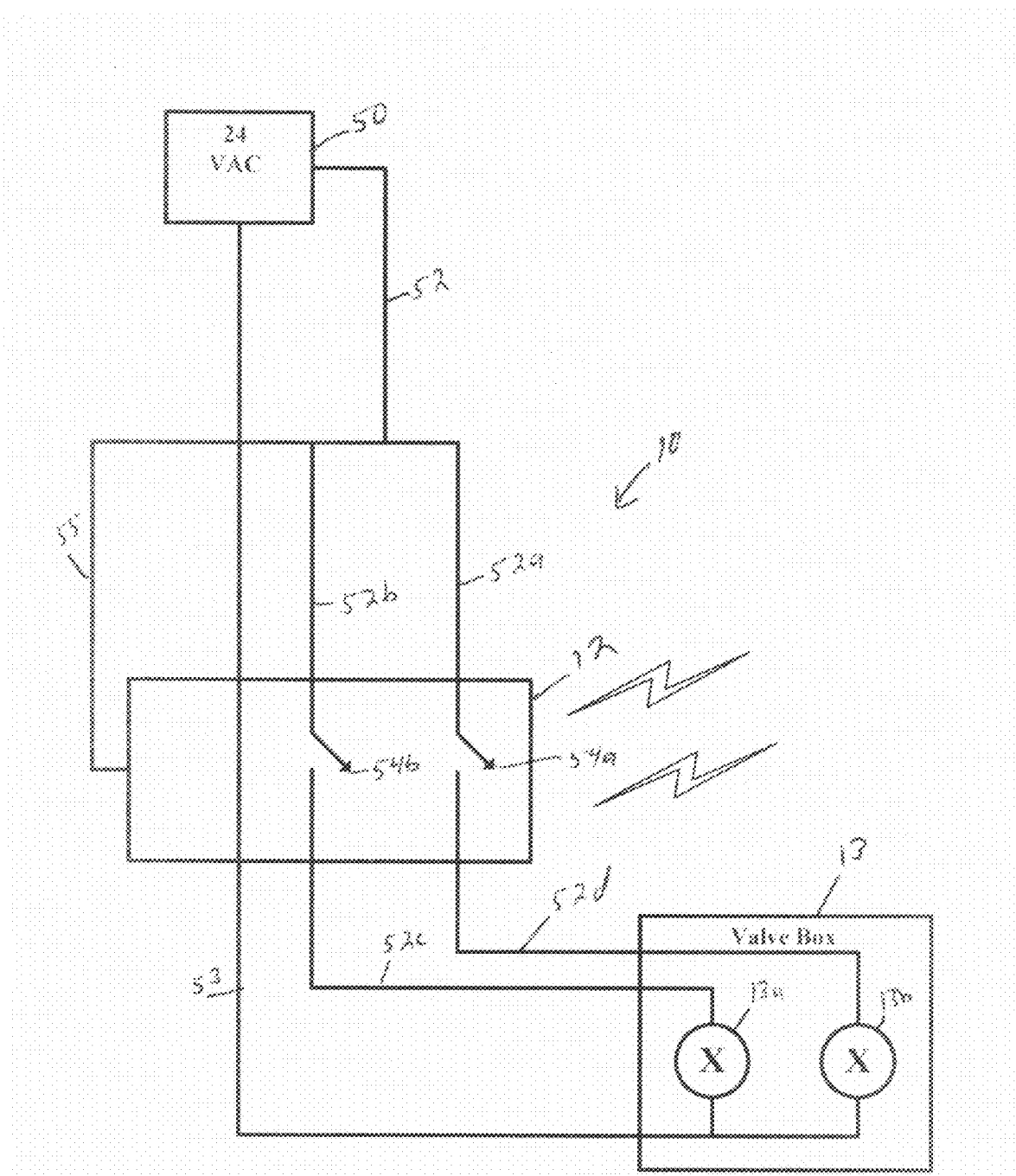
FIG. 17 is a schematic diagram of an irrigation control system with a wireless irrigation controller.

In the wireless irrigation controller system 10 of FIG. 17, the same interrupter hardware is used but the inputs to the irrigation interrupter 12 are always on, i.e. the irrigation interrupt 12 is now in control and irrigation will occur under the direct control of the wireless interrupter 12 based on soil moisture data. Different firmware is necessary, but the hardware is identical with only minimal changes in the wiring.

In both systems, power for the irrigation interrupter 12 is drawn directly off the 24 VAC eliminating the need for a separate power supply.

The system 10 is capable of operating with soil moisture only wireless soil sensors 21 with integrated two-way wireless telemetry, sensor firmware, an irrigation interrupter/controller (Controller) and controller firmware. The wireless soil sensors consist of a soil moisture only sensor, wireless two-way telemetry, microcontroller, and at least some non-volatile memory, and are preferably battery powered. These components are integrated into one physical package (no cabling) and the wireless soil sensor 21 is buried in strategic locations to monitor soil moisture conditions. The sensor firmware manages making sensor measurements, transmitting them to the controller, receiving controller commands, and power-management (putting system to sleep). The controller 11 preferably consists of two-way wireless telemetry compatible with the wireless soil sensors 21, a microcontroller, non-volatile memory, a user input (preferably a four or five way wheel), display (preferably 36 character two line LCD), and circuitry for opening or closing switches for irrigation zones (switch in an open position is over-riding irrigation). In existing irrigation systems and for use with an already installed controller, the wireless controller 11 is spliced into existing wiring close to an existing irrigation controller. In replacing an existing irrigation controller or in new installations, the wireless controller 11 is directly connected to irrigation zone wiring. The controller firmware allows collection of wireless telemetry of soil moisture data, "commissioning" of new wireless soil sensors 21, i.e. associating a wireless soil sensor 21 with an irrigation zone and an installation, setting irrigation thresholds, etc.

All of the components preferably operate over a temperature range of −20 to 70° C. (with the exception of the display which is operable over 0 to 50° C.) and are capable of storage over −20 to 70° C. All components preferably are Human Body Model ESD resistant but not lightning resistant. Wireless soil sensors 21 are preferably fully waterproof while the interrupters 12 preferably only have a low level of splash-proofing. For the purposes of determining battery shelf life in the wireless soil sensors 21, a temperature under 40 C is assumed (temperature, depending on battery technology, can greatly impact self discharge rates). Wireless telemetry range of approximately 100-200 feet is preferred. The range is achieved at depths of up to 12 inches and in moderate clutter (vegetation, slight topography, through garage wall, etc.). A wireless soil sensor 21 is preferably installed at least as close as 3 inches from soil surface for monitoring soil moisture in shallow rooting turf. The package of the wireless soil sensor is preferably no larger than 2"×2"×8" (ideally 1.5"×1.5"×6"). A bulky package is difficult to install (particularly at shallow depths), disrupt soil environment, and a turn-off to consumers. A non-volatile memory is preferred. Timekeeping is accurate to within +/−2% which allows the wireless soil sensors 21 to wakeup at on a regular schedule, timing for I2C commands, as well as scheduling sensor "listen" windows for wireless receive modes.

The wireless soil sensor 21 is capable of receiving simple operational parameters wirelessly from a controller 11 or an interrupter 12, which allows the controller 11 or the interrupter 12 to set reporting interval, selection of adaptive algorithms, etc.

A procedure for re-programming the wireless soil sensors 21 after production is included in order to allow for changes encountered in debugging or upgrades. Alternatively, it can be through a programming header in the battery or by some other wireless programming option.

The wireless soil sensor 21 is preferably able to detect imminent battery, to prevent the wireless soil sensors 21 from failing suddenly with no warning or begin to operate intermittently reflecting battery temperature and other variable as well as possibly giving corrupted data that may result in incorrect irrigation decisions.

The sensor firmware is capable of executing and reading I2C commands. Analog sensor requires I2C commands to control oscillator and make A/D measurements. I2C commands need to be executed sequentially according to a sloppy timing of about +/−3 mS over 100 mS. I2C can operate anywhere from 20 to 200 KHz. The sensor firmware is able to perform simple calculations like conversion of raw A/D values into soil moisture which requires simple functions-addition, subtraction, division, polynomials but no log, trig, etc. functions. The sensor firmware is capable of going into a very low power mode between set measurement interval with routines to wake up at end of interval which may range from 1-100 min. which is set in a non-volatile configuration file which can be modified by interrupt controller. After measurement is complete, soil moisture data needs to be sent to interrupt controller 11.

The sensor firmware preferably has a static soil moisture mode. An operational mode that allows the wireless soil sensor 21 to wake up, measure soil moisture, and if a change in soil moisture from the last wirelessly reported measurement does not exceed a settable threshold, return to a sleep mode without sending data. This threshold value, as well as whether this feature is enabled, preferably resides in a non-volatile configuration file which can be modified by the interrupt controller 11. The wireless soil sensor 21 preferably transmits a new reading once every six hours regardless of soil moisture changes to confirm operation.

The wireless soil sensor 21 preferably has a default mode firmware upon power restart for the sensor firmware, which allows a wireless soil sensor 21 to be commissioned, i.e. assigned to a specific irrigation interrupter to allow for resolving sensors from a close neighbors residence. In addition, commissioning must be flexible to allow for a change in assigned interrupt controller 11 in the future or if commissioning is lost.

A wireless soil sensor 21 is preferably capable of a listening mode in a power efficient manner for receiving changes to the configuration file wirelessly from the interrupt controller 11 with a maximum file size of 100 bytes at least once a month without degrading three year sensor battery life. The wireless soil sensor 21 preferably has the ability to download full operating firmware.

On a regular schedule (about once every six hours) the wireless soil sensor 21 preferably provides in addition to the soil moisture value, diagnostics such as battery voltage, and raw measured values not to exceed an additional 25 bytes. This data is used to assess performance and for diagnosis of bugs or sensor failure.

If the raw A/D values used to determine soil moisture data are out of normal ranges, the wireless soil sensor 21 preferably sends a "Bad Data" even if the computed soil moisture value appears reasonable. This helps detect failed wireless soil sensors 21 and prevent bad control actions.

The irrigation interrupter 12 is capable of turning on and off AC current up to 700 mA continuously at 70 C for each irrigation zone from an AC voltage range of 16 to 34 volts with no more that 1V in drop across switching circuitry. Switching circuitry is not damaged by inductive transients generated by turn off of valve solenoids.

Regardless of whether the interrupt controller 11 is allowing or blocking irrigation, the interrupt controller 11 can detect the presence of an AC voltage (generated by irrigation controller 11 to initiate an irrigation). This feature allows for calculations of savings such as % of scheduled irrigation events that were canceled by system.

The hardware for the irrigation interrupter 12 is preferably resistant to moderate ESD and transients that may enter system through 24 VAC transformer in order to be reliable.

The interrupt controller 11 draws power directly from nominal 24 VAC transformer to avoid having to use a separate power supply with a maximum current draw of 100 mA. The interrupt controller 11 operates correctly with an AC input varying from 16 to 34 VAC to account for AC mains voltage of 84 to 130 VAC (typical specified level of AC power seen in a household) and variation in transformer output with load.

The interrupt controller 11 is capable of operating in typical residential systems which have between four and eight zones. More sophisticated systems could be addressed by using multiple units.

The interrupt controller 11 is preferably capable of a log for the last 30 days of soil moisture readings for eight zones at 10 minute interval as well as whether an irrigation event is occurring, and whether it has been interrupted at 1 minute intervals in non-volatile memory. The log is preferably structured so accurate date and time is available for data record. This feature is good for both debugging purposes but also in allowing the system to display to the user the amount of water saved thus justifying the product.

Firmware responds as gracefully as possible to problems. For instance, if soil moisture data is out of range or uC lockup (possibly detected by watchdog circuit) irrigation proceeds according to the irrigation controller 11 (i.e. no interrupt). If an irrigation interrupter 12 is operating as a wireless irrigation controller (no standard irrigation controller), the system 10 should default to no irrigation. Failure modes give obvious indication of problems.

Ample code space is preferably reserved to allow for extensive additional features in the future. All user settable configurations are preferably stored in non-volatile memory so as to allow for seamless recovery from lockup or loss of power. Preferably, a real time clock has the ability to keep time after power loss for up to 1 month.

The interrupter firmware is capable of generating a user water savings report for the last day, week, and month (i.e. percent of scheduled irrigation that was interrupted) by zone and as a whole for all eight zones as well as total run time per zone.

A process is developed to allow sensors upon installation or system expansion to be assigned to a particular irrigation zone for a particular irrigation interrupter. The process needs to be flexible enough to allow for replacement of failed wireless soil sensors 21 as well. This allows the system 10 to be used with neighboring installations without confusion as well as assigning the right sensor to the right zone.

A user sets, for each zone, the maximum soil moisture level that will terminate an irrigation event. There is also a settable hysteresis, Y, i.e. if during a single scheduled irrigation event the soil moisture rises about the threshold X and irrigation is stopped, it would not begin again until level fell to X-Y. This prevents valves from turning on and off rapidly when approaching the threshold. When new irrigation event occurs, the threshold defaults back to X.

A hold feature allows a user to hold current conditions going forward (i.e. take last soil moisture readings and apply as thresholds).

A show current status mode for the interrupt controller 11 defaults to when no keypad entry has occurred for a minute or so and shows zone by zone-threshold, last soil moisture data, irrigation is being attempted, and if irrigation is being interrupted.

The save configuration allows up to six configurations to be saved, named, and recalled (for all zones thresholds, hysteresis, adaptive algorithms on or off, etc.). This allows for summer and winter settings, etc.

A disable setting is where all zones are enabled and the system is under control of the irrigation controller 11 solely, i.e. the interrupter 12 allows valves 13a and 13b to be on at all times when the standard irrigation controller 11 schedules irrigation regardless of the soil moisture data. This is a "safety mode" so that if there are critical problems, the user is not forced to reconfigure things to keep the grass from dying.

A bump feature allows a user to "bump" up or down all thresholds equally at an approximately 0.5% water by volume increment (allows for quick adjustment for hot weather or other reasons), which revert to previous settings after 1 days unless user selects to apply them permanently.

The firmware is preferably capable of detecting missing or out of range soil moisture and low battery conditions and display warning.

A wireless irrigation controller mode allows the irrigation interrupter 12 to function as full soil moisture data driven irrigation controller 11 without the use of a standard irrigation controller 11. Essentially all of the features of a standard irrigation controller 11 are implemented such as scheduling irrigation times, valve run-times, etc. These scheduled events are subjected to the same "interrupt" schemes as the irrigation interrupter 12 based on soil moisture data.

When water is applied to the soil the wireless soil sensors 21 report the increase in moisture content but also look at the tail off in moisture levels when irrigation ceases. In cases of significant overwatering, there is a sharp spike in moisture levels followed by a sharp fall after irrigation ceases. This is due to the soil essentially being so wet it "free drains" below the root zone (thus wasting the water). The present invention implements algorithms to monitor this and adjust irrigation events to eliminate this wasteful practice allowing the system to essentially configure itself over time. The wireless soil sensor 21 is preferably directly integrated with a radio and microcontroller. It also preferably has a sleeve that fits over the sensor that the user removes to turn it on. It also preferably has an optional microcontroller generated clock signal to avoid having to use a separate oscillator for the conductivity measurement. It also preferably has the same RF frequency the radio uses to eliminate having to use a separate oscillator for the soil moisture measurement. It also preferably uses "spread spectrum oscillators" to achieve FCC compliance. It also preferably has sensor components that are currently PCB may be made out of conducting plastic formulations simplifying assembly, improving aesthetics, and reducing costs.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for improving a communication range and communication reliability of an antenna for a wireless soil sensor buried below the surface of a land area, the method comprising:
   activating a wireless sensor;
   measuring a plurality of soil electrical properties for the land area;
   transmitting data from the wireless sensor to at least one receiver above the surface of the land area at a plurality of switchable antenna configurations;
   monitoring a signal property of each transmission of data for each of the plurality of switchable antenna configurations;
   repeating the above steps every predetermined number of sensor transmission cycle;
   creating a map of the signal property for the plurality of switchable antennal configurations;
   providing the map to each of a plurality of sensor nodes;
   determining from the map the most favorable antenna configuration for the position of the node;
   configuring the sensor node to the most favorable antenna configuration; and
   transmitting data from the node.

2. The method according to claim 1 wherein the predetermined number of sensor transmission cycles is sixty.

3. The method according to claim 1 wherein the plurality of soil electrical properties comprises soil conductivity and soil dielectric constant.

4. The method according to claim 1 wherein the map is a two dimension map of soil conductivity and soil dielectric constant.

5. The method according to claim 1 wherein the signal property is received signal strength.

6. The method according to claim 1 wherein the land area is a golf course.

7. A system for improving a communication range and communication reliability of an antenna for a wireless soil sensor buried below the surface of a land area, the system comprising:
   a plurality of wireless sub-surface sensors, each of the plurality of wireless sub-surface sensors capable of monitoring soil conductivity and soil dielectric constant, each of the plurality of wireless sub-surface sensors comprising a configuration switchable antenna for transmitting and receiving data to and from above ground, a processor and a battery, wherein the data comprises the soil conductivity and soil dielectric constant;
   a receiver for receiving and transmitting data to the plurality of wireless sub-surface sensors, the receiver also monitoring signal strength from each of the plurality of wireless sub-surface sensors based on a plurality of switchable antenna configurations; and
   a control engine, the control engine receiving the data from the receiver, the control engine having a processor configured to create a two dimensional map of the signal property for the plurality of switchable antenna configurations based on soil conductivity and soil dielectric constant.

8. The system according to claim 7 wherein each of the plurality of wireless sub-surface sensors comprises a first plurality of sensors and a second plurality of sensors, each of the first plurality of sensors positioned within an upper soil and capable of monitoring an upper soil conductivity and an upper soil dielectric constant, each of the second plurality of sensors positioned within a lower soil and capable of monitoring a lower soil conductivity and a lower soil dielectric constant.

9. The system according to claim 7 wherein each of the plurality of wireless sub-surface sensors transmits and receives data at a communication frequency of 2.4 GigaHertz.

10. The system according to claim 7 wherein each of the plurality of wireless sub-surface sensors comprises a probe conducting structure, a circuit comprising a high frequency oscillator for applying a electrical stimulus to the probe structure, a reference capacitor connected in series to the high frequency oscillator, and a voltage meter located between the high frequency oscillator and the reference capacitor.

* * * * *